United States Patent
Moriyama et al.

(10) Patent No.: US 9,173,724 B2
(45) Date of Patent: Nov. 3, 2015

(54) OCCLUSAL ADJUSTMENT SYSTEM

(75) Inventors: Takeshi Moriyama, Kyoto (JP); Yusei Kadobayashi, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 676 days.

(21) Appl. No.: 13/168,234

(22) Filed: Jun. 24, 2011

(65) Prior Publication Data

US 2012/0003604 A1 Jan. 5, 2012

(30) Foreign Application Priority Data

Jun. 25, 2010 (JP) ................................ 2010-145274

(51) Int. Cl.
| | |
|---|---|
| *A61C 9/00* | (2006.01) |
| *A61C 13/00* | (2006.01) |
| *A61C 13/10* | (2006.01) |
| *A61C 11/00* | (2006.01) |

(52) U.S. Cl.
CPC ......... *A61C 13/0024* (2013.01); *A61C 13/0004* (2013.01); *A61C 13/0006* (2013.01); *A61C 13/10* (2013.01); *A61C 11/00* (2013.01)

(58) Field of Classification Search
CPC ........... A61C 13/0004; A61C 13/0024; A61C 13/097; A61C 3/02; A61C 19/05
USPC ........ 433/68–71; 264/17–18; 700/97–98, 118
See application file for complete search history.

(56) References Cited

U.S. PATENT DOCUMENTS

| | | | |
|---|---|---|---|
| 4,264,308 A * | 4/1981 | Tanaka .......................... | 433/223 |
| 6,533,581 B1 * | 3/2003 | Moenckmeyer .............. | 433/197 |
| 2002/0150859 A1 | 10/2002 | Imgrund et al. | |

(Continued)

FOREIGN PATENT DOCUMENTS

| | | |
|---|---|---|
| EP | 1 293 174 | 3/2003 |
| JP | 2010-17467 | 1/2010 |

(Continued)

OTHER PUBLICATIONS

Extended European Search Report (in English language) issued Aug. 22, 2012 in corresponding European Patent Application No. 11 00 5211.

(Continued)

*Primary Examiner* — Cris L Rodriguez
*Assistant Examiner* — Matthew Nelson
(74) *Attorney, Agent, or Firm* — Wenderoth, Lind & Ponack, L.L.P.

(57) ABSTRACT

Occlusal-surface shape data and occlusal-surface position data of dentures are acquired on a dentist side, and the occlusal-surface shape data and the occlusal-surface position data are then transmitted to a grinding data provider side. Maxillomandibular occlusal state data is reproduced from the occlusal-surface shape data and the occlusal-surface position data on the grinding data provider side. A maxillomandibular occlusal adjustment portion is determined by changing a maxillomandibular occlusal vertical dimension on the grinding data provider side. Cutting data including the maxillomandibular occlusal adjustment portion and the occlusal-surface position data is prepared on the grinding data provider side, and the cutting data is transmitted to the dentist side. An occlusal adjustment is carried out on the dentist side by cutting the dentures by a grinding machine based on the cutting data.

10 Claims, 28 Drawing Sheets

(56) References Cited

U.S. PATENT DOCUMENTS

| | | |
|---|---|---|
| 2003/0123943 A1 | 7/2003 | Hamada |
| 2005/0023710 A1* | 2/2005 | Brodkin et al. ................ 264/16 |
| 2005/0095552 A1 | 5/2005 | Sporbert et al. |
| 2005/0095562 A1 | 5/2005 | Sporbert et al. |
| 2005/0118555 A1 | 6/2005 | Sporbert et al. |
| 2005/0153255 A1* | 7/2005 | Sporbert et al. ................ 433/24 |
| 2007/0190492 A1* | 8/2007 | Schmitt ........................ 433/213 |
| 2008/0050700 A1* | 2/2008 | Weber et al. ............... 433/202.1 |
| 2008/0311537 A1* | 12/2008 | Minagi et al. ................... 433/68 |
| 2009/0042167 A1* | 2/2009 | Van Der Zel ................. 433/215 |
| 2009/0068617 A1* | 3/2009 | Lauren ......................... 433/213 |
| 2009/0298017 A1* | 12/2009 | Boerjes et al. ................ 433/214 |
| 2011/0276159 A1* | 11/2011 | Chun et al. ..................... 700/98 |

FOREIGN PATENT DOCUMENTS

| | | |
|---|---|---|
| JP | 2010-502300 | 1/2010 |
| JP | 2011-517801 | 6/2011 |
| WO | 03/092536 | 11/2003 |
| WO | WO 03092536 A1 * | 11/2003 |
| WO | 2008/027771 | 3/2008 |
| WO | 2009/105684 | 8/2009 |

OTHER PUBLICATIONS

Japanese Office Action (OA) issued Sep. 2, 2014 in corresponding Japanese Patent Application No. 2011-141998.

* cited by examiner

OCCLUSAL ADJUSTMENT SYSTEM

BACKGROUND OF THE INVENTION (1) Field of the Invention

The present invention relates to a denture occlusal adjustment system in which preparation of dentures in a denture-production process is performed by a dentist or a dental technician and an occlusal adjustment in the process is performed by a special contractor.

(2) Description of Related Art

A denture-production process generally includes the steps of preparing wax dentures using artificial teeth and wax; replacing a plate made of wax with acrylic resin for denture plate by a lost-wax process to prepare pre-occlusal adjustment dentures, and subjecting the pre-occlusal adjustment dentures to an occlusal adjustment.

In the occlusal adjustment step, the pre-occlusal adjustment dentures are attached to an articulator. The acrylic resin for denture plate has a property of slightly contracting when being polymerized (hardened) and, in many cases, causes a small increase in height of occlusion. In order to correct this, it is necessary to perform a correction adjustment of the occlusion once again.

The occlusion state when the dentures are occluded is confirmed. Then, the occlusion surfaces of artificial teeth are adjusted by grinding to allow the artificial teeth to occlude evenly in horizontal direction. An articulating paper, such as 12-micron carbon paper, is placed between the occluded teeth and the contact portions between the teeth are marked by color. If occlusion is poor, dentures particularly the full dentures are not stable.

However, it is not better to properly grind a portion that strongly contact with the opposite portion. It is necessary to grind and adjust the contact portion while a force-exerting direction is considered so that the dentures will be stabilized while being occluded.

Next, occlusion when jaws are moved in the right-and-left and forward-and-backward directions, or when so-called teeth gnashing is performed, is adjusted. By using an articulating paper with color different from the color of the former articulating paper, occlusion is adjusted by grinding while harmonious occlusion of front and back teeth is considered. Although there are various theories about occlusion, occlusion is adjusted by grinding in the style of "full balanced occlusion" where all the teeth can slidably contact with the corresponding teeth even when the jaw are moved in any direction (teach gnashing).

Grinding is performed so that the dentures are stably occluded when the jaw is moved in the left direction or in the right direction. Occlusion when the jaw is moved forward is similarly adjusted by grinding. A micro-order fine work is repeated.

An occlusal adjustment work is a work for grinding an occluded surface. Specifically, the occlusal adjustment work is a work for marking (coloring) contact portions of the upper and lower jaws in the occlusal surface, which is an occluded surface, by using a carbon paper or the like and grinding such portions little by little. In order to do this work correctly, even an expert may take one or two hours for the work.

The articulator reproduces just an average movement of jaws. Therefore, an occlusal adjustment is also based on theoretical average values. However, the occlusal adjustment can be performed within the minimum range in a dental clinic when dentures are actually applied to a patient by correctly adjusting the occlusion to the theoretical average values. Patient's sense on incongruity, pain, or the like can be minimized. This means that an occlusal adjustment is the most important work in the denture-production process.

Conventionally, the preparation of dentures has been performed by teamwork of a dentist and a dental technician. Among the steps of the denture-production process, the occlusal adjustment requires well knowledge and experience. Thus, the occlusal adjustments have been complicated and difficult works even for dentists and dental technicians through a trial and error process.

SUMMARY OF THE INVENTION

The present invention relates to a denture occlusal adjustment system in which preparation of dentures is performed by a dentist or a dental technician and an occlusal adjustment is performed by a special to shorten an occlusal adjustment work while obtaining correct occlusion.

According to a first aspect of the present invention, a denture occlusal adjustment system includes:

means for acquiring occlusal-surface shape data and occlusal-surface position data of dentures on a dentist side;

means for transmitting the occlusal-surface shape data and the occlusal-surface position data from the dentist side to a grinding data provider;

means for reproducing a maxillomandibular occlusal state data on the grinding provider side from the occlusal-surface shape data and the occlusal-surface position data received from the dentist side;

means for determining a maxillomandibular occlusal adjustment portion by changing a maxillomandibular occlusal vertical dimension on the grinding data provider side;

means for preparing cutting data including the occlusal adjustment portion data and the occlusal-surface position data on the grinding data provider side;

means for transmitting the cutting data from the grinding data provider side to the dentist side; and means for performing an occlusal adjustment by cutting the dentures by a grinding machine based on the cutting data on the dentist side.

According to a second aspect of the invention, a denture occlusal adjustment system includes:

means for acquiring maxillomandibular impression data with silicone or wax on the dentist side;

means for transmitting the impression data from the dentist side to the grinding data provider side;

means for reproducing a maxillomandibular occlusal state on the grinding data provider side from the impression data received from the dentist side, means for determining a maxillomandibular occlusal adjustment portion by changing a maxillomandibular occlusal vertical dimension on the grinding data provider side;

means for preparing cutting data including the occlusal adjustment portion data and the occlusal-surface position data on the grinding data provider side;

means for transmitting the cutting data from the grinding data provider side to the dentist side; and means for performing an occlusal adjustment by cutting the dentures by a grinding machine based on the cutting data on the dentist side.

Preferably, the denture occlusal adjustment system of the first or second aspect further includes:

means for creating image data that represents the occlusal adjustment portion, means for transmitting the image data from the grinding data provider side to the dentist side; and means for confirming the image data received from the grinding data provider side on the dentist side and transmitting a signal whether the image data is accepted or not, wherein when the means for determining the occlusal adjustment portion receives a signal of unacceptable, the means for determining the occlusal adjustment portion determines a maxillomandibular occlusal adjustment portion by further changing a maxillomandibular occlusal vertical dimension; and when the means for creating cutting data receives a signal of acceptable, cutting data including the occlusal adjustment portion data and the occlusal-surface position data is prepared.

Preferably, the denture occlusal adjustment system of the first or second aspect further includes:

means for notifying a change in occlusal vertical dimension when the dentist side does not accept the image data, wherein the means for determining the occlusal adjustment portion determines the maxillomandibular occlusal adjustment portion at the changed occlusal vertical dimension when the means for notifying a change in occlusal vertical dimension notifies a change in occlusal vertical dimension.

Preferably, the denture occlusal adjustment system of the first or second aspect further includes: means for charging for provision of the cutting data on the grinding data provider when the means for transmitting the cutting data transmits the cutting data.

Preferably, the denture occlusal adjustment system of the first or second aspect further includes: means for charging for provision of the image data and the cutting data on the grinding data provider side, when the means for transmitting the signal of acceptable or signal of unacceptable transmits a signal of acceptable, or when the means for transmitting the cutting data transmit cutting data.

According to a third aspect of the present invention, the denture occlusal adjustment system further includes:

means for acquiring occlusal-surface shape data and occlusal-surface position data of occlusion-adjusted dentures on the dentist side;

means for transmitting the occlusal-surface shape data and the occlusal-surface position data of the occlusion-adjusted dentures from the dentist side to a grinding data provider;

means for creating confirmation image data which can confirm whether a grinding-required portion is ground by, on the grinding data provider side, laying the occlusal-surface shape data and the occlusal-surface position data of the occlusion-adjusted dentures received from the dentist side on cutting data of the occlusal adjustment portion;

means for confirming whether the grinding-required portion is ground on the grinding data provider side;

means for transmitting the confirmation image data from the grinding data provider side to the dentist side when confirming that the grinding-required portion is ground;

means for confirming whether the confirmation image data received from the grinding data provider side by the dentist side has any problem;

means for notifying the center side from the dentist side that no problem in the confirmation image data is confirmed;

means for creating cutting data of a re-occlusal adjustment portion on the grinding data provider side when it is confirmed that the grinding-required portion is ground;

means for transmitting the cutting data from the grinding data provider side to the dentist side;

means for confirming whether re-occlusal adjustment is required based on the cutting data on the dentist side; and means for notifying that no need of re-occlusal adjustment is confirmed when the dentist side confirms no need of re-occlusal adjustment, wherein when means for confirming whether re-occlusal adjustment is required based on the cutting data on the dentist side confirms that a re-occlusal adjustment is required, an occlusal adjustment is performed by cutting the dentures by a grinding machine based on the cutting data on the dentist side.

Alternatively, the denture occlusal adjustment system of the third aspect of the present invention further includes:

means for acquiring occlusal-surface shape data and occlusal-surface position data of occlusion-adjusted dentures on the dentist side;

means for transmitting the occlusal-surface shape data and the occlusal-surface position data of the occlusion-adjusted dentures from the dentist side to the grinding data provider side;

means for creating confirmation image data which can confirm whether a grinding-required portion is ground by, on the grinding data provider side, laying the occlusal-surface shape data and the occlusal-surface position data of the occlusion-adjusted dentures received from the dentist side on cutting data of a occlusal adjustment portion, means for transmitting the confirmation image data from the grinding data provider side to the dentist side;

means for diagnosing whether the confirmation image data received from the grinding data provider side by the dentist side has any problem;

means for notifying from the dentist side that it is diagnosed as no problem in the confirmation image data when it is diagnosed as no problem in the confirmation image data;

means for creating cutting data of a re-occlusal adjustment portion on the grinding data provider side when it is diagnosed as a problem in the confirmation image data; means for transmitting the cutting data from the grinding data provider side to the dentist side;

means for confirming whether re-occlusal adjustment is required based on the cutting data on the dentist side; and means for notifying that no need of re-occlusal adjustment is confirmed when the dentist side confirms no need of re-occlusal adjustment, wherein when means for confirming whether re-occlusal adjustment is required based on the cutting data on the dentist side confirms that a re-occlusal adjustment is required, an occlusal adjustment is performed by cutting the dentures by a grinding machine based on the cutting data on the dentist side.

According to a fourth aspect of the present invention, in the denture occlusal adjustment system of any of the first to third aspect, the means for acquiring occlusal-surface shape data and occlusal-surface position date further includes, in addition to the occlusal-surface shape data and the occlusal-surface position data, jaw-movement data and reference point data that makes a connection between jaw-movement data and the occlusal-surface shape data.

The jaw-movement data is preferably setting data of an articulator including condylar distance, distance between upper arch and the lower arch, sagittal condylar path inclination, balancing-side lateral condyle path angle, immediate side shift, angle of the working side lateral condyle path, sagittal incisal path inclination, and lateral incisal path guide angle.

The denture occlusal adjustment system further includes:

means for calculating a position of reference point of artificial tooth-shape data to be used as a standard by making a verification between the acquired occlusal-surface shape data of artificial tooth and the artificial tooth-shape data to be used as a standard, wherein the means for transmitting the occlusal-surface shape data and the occlusal-surface position data from the dentist side to a grinding data provider transmits the artificial tooth-shape reference point data as the occlusal-surface shape data, further includes:

means for reconstructing occlusal-surface shape data of artificial tooth and verifying the artificial tooth-shape reference point data with a reference point of artificial tooth-shape data to be used as a standard on the grinding data provider side.

According to the first aspect of the invention, preparation of dentures itself in a denture-production process is performed by a dentist or a dental technician and an occlusal adjustment in the process is performed by a special contractor. Thus, correct occlusion can be obtained while occlusal adjustment work is shortened.

Data is delivered and received on a network. Thus, grinding data can be confirmed without large influence of system requirements of a client PC on the dentist side. A new grinding system can be obtained freely.

Since calculation of occlusal adjustment data is performed on the grinding-data provider, load on the client PC on the dentist side can be reduced.

By requesting occlusal adjustment information from an outside grinding-data provider, it is possible to charge for every denture, and an initial investment on the dentist side can be reduced.

Before charging, it is possible to confirm whether the occlusal adjustment using any aspect of the present invention should be performed by delivering and receiving occlusal adjustment data. Thus, the dentist side, which is a user, can be prevented from needless charging.

Since the state after the occlusal adjustment can be virtually confirmed and the state after the occlusal adjustment can be confirmed in detail on a screen, the configuration of the articulator can be reconfigured.

Since the cross-section and extended state of the occlusal surface can be confirmed before the occlusal adjustment, the occlusal adjustment can be prevented from failing.

According to the second aspect of the invention, in addition to the advantageous effects of the first aspect, a slight displacement of the inter-cuspal position produced when equipped in a buccal cavity can be diminished. Thus, the more optimal occlusal relationship can be reproduced. A maxillomandibular occlusal state can be obtained without load to a patient.

In the case of dental inlays and onlays where part of tooth is filled with prosthesis, the prosthesis has been made by using a jaw model of one jaw.

However, in consideration of a relationship with opposing teeth, an occlusal adjustment may be performed to prepare better denture. In this case, it has been also necessary to create the jaw model of the opposite side and such a jaw-model production work has been needed. Thus, it has been skipped. Furthermore, the occlusal adjustment was one using a carbon paper and has not been easily performed. Thus, it has been intended to be avoided.

According to the second aspect of the present invention, the production of a jaw model for a prosthetic portion is necessary; however, there is no need of preparing an opposite jaw model.

In other words, the form of an occlusal surface of a portion, where prosthesis is formed, and the form of the opposite occlusal surface are molded in a silicone mold using a "silicone tray with reference point (illustrated in the figure). Impressions and reference points are read by a common scanner and provided as "data representing a positional relationship between upper and lower jaws" for performing the occlusal adjustment.

The occlusal surface of a portion, where the silicone-molded prosthesis is formed, is prepared. Then the prosthesis is prepared and read with the scanner to give "prosthesis data". Then, grinding data can be calculated based on the above "data representing a positional relationship between upper and lower jaws" and "prosthesis data".

According to the third aspect of the present invention, it is possible to confirm whether dentures are ground by CAM according to CAM data.

Thus, a dentist and a grinding-data provider can confirm whether the grinding of dentures is performed correctly. The grinding-data provider clearly recognizes the state of confirming by the dentist. The grinding-data provider also clearly recognizes the states before and after the grinding by using image data after the actual grinding. If the grinding is performed wrong, a warning can be given.

The image data (including 3D-data) before and after grinding may be advantageously used for informed consent to a patient.

In addition, a patient's occlusal state can be left on record and can be used as important data when the optimal denture for the patient is prepared.

According to the fourth embodiment, the amount of data to be transmitted and received between the dentist side (dentist or dental technician) and the grinding-data provider can be reduced. Furthermore, the amount of data of the required portions to be stored can be reduced. Thus, data management can be facilitated.

DETAILED DESCRIPTION OF PREFERRED EMBODIMENTS

Figure 1:
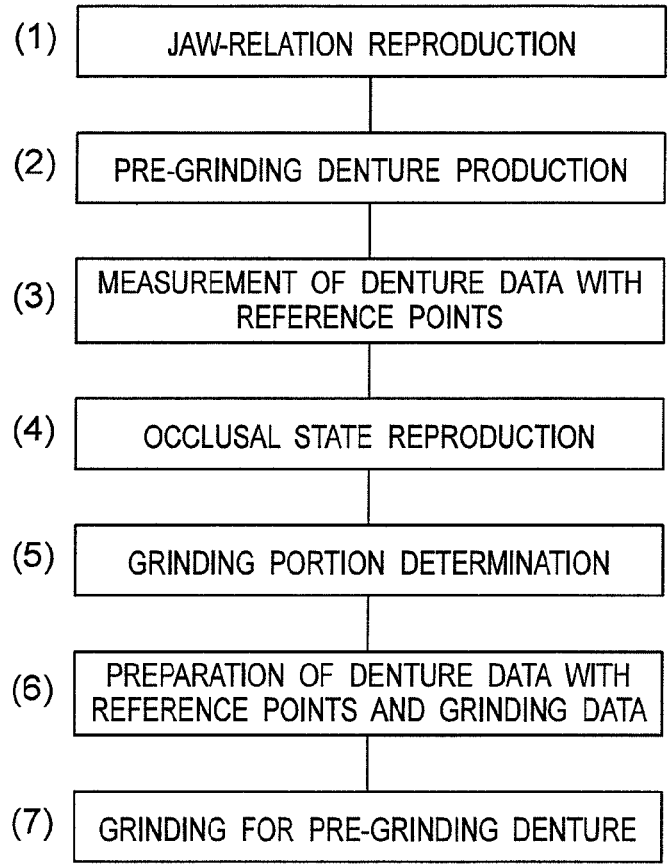
FIG. 1 is a flowchart illustrating a denture-grinding method according to the present invention.

Hereafter, embodiments of the present invention will be described with reference to the attached drawings.

A typical process for producing a denture is as follows:

1. An intraoral form of a patient is taken to prepare an impression.
2. An intraoral model of the patient is made of plaster using the impression and a constituent resin base plate is prepared on the model.
3. Wax is poured into a mold form and fixed in the shape of an arch. The wax is then mounted on the base plate to form a wax rim on which artificial tooth are arranged. A combination of this wax rim and the base plate is referred to as a bite plate.
4. The bite plate is applied to a patient to take a bite form of the patient.
5. Maxillary and mandibular models equipped with the bite plate is attached to an articulator to reproduce an occlusion state on the articulator.
6. Artificial tooth suitable for the patient are selected and maxillary anterior artificial teeth are arranged first on the maxillary wax rim and then mandibular anterior artificial teeth on the mandibular wax rim.
7. The maxillary height is slightly increased by adjusting an incisal pole of the articulator and mandible and maxillary molar artificial teeth are then arranged on the wax rim.
8. The incisal pole of the articulator is returned to the original state and an occlusal adjustment for grinding high portions is performed. In the occlusal adjustment, an articulating paper is sandwiched between the upper jaw and the lower jaw and a portion that strongly comes into contact with the opposite portion is ground.
9. A cervix (neck portion) state and a gingival regional state of the anterior teeth are reproduced.
10. The denture model with artificial teeth arranged on the bite plate is applied to the buccal cavity of the patient on a trial basis and information about required correction is then obtained.
11. Portions which should be corrected are corrected according to the information.
12. The denture model is separated in a flask (frame) and embedded in plaster and solidified.
13. The flask is heated to soften the wax of the denture model and the flask is removed to melt the wax, resulting in a mold.
14. A separation material is applied to the plaster portion of the mold and resin for denture plate (synthetic resin)) is then poured into the mold. The upper and lower mold forms are combined together and then pressed by a press.
15. Excessive resin is removed and the upper and lower frames are set, followed by being subjected to heat to harden the resin.
16. The mold forms are removed and the plaster is then taken out to scrape out the denture.
17. The denture is attached to the articulator again and occlusal imbalance caused by contraction occurred in resin hardening is then corrected. Articulating paper is used in occlusal correction.
18. Occlusion when the jaw is moved back and forth and left and right is adjusted with an articulating paper (this adjustment is a last occlusal adjustment and called grinding).
19. Removing burrs from the resin, polishing is performed.

In the step of producing a denture, the intraoral form is taken, the wax rim is formed, the artificial teeth are arranged, and the wax is replaced with the resin by a lost-wax process. In this case, the contraction of the resin causes a positional displacement of artificial teeth and interference occurs when the artificial teeth are bitten as dentures by the upper and lower jaws. The grinding is the adjustment of such an interference portion. Even if the occlusion is correctly performed on the dentures, the grinding may be performed to change the occlusal relationship depending on the status of the buccal cavity of the patient. The adjustment is performed in corporation with the movement of the jaws of the patient. According to the present invention, a series of these operations is performed using a program.

Here, in the case of a denture-grinding method, full dentures are preferable. Alternatively, partial dentures may be also used even in the case where the upper and lower jaws are a combination of dentures.

1. Denture Grinding Method

The denture-grinding method of the present invention includes the following processes as illustrated in FIG. 1.

(1) Jaw-relation reproduction step
(2) Pre-grinding denture production step
(3) Measurement step for denture data with reference points
(4) Occlusal state reproduction step
(5) Grinding portion determination step
(6) Preparation step for denture data with reference points having grinding data
(7) Grinding step for pre-grinding dentures (1) The jaw-relation reproduction step in which the jaw-relation reproduction conditions that can reproduce the conditions of the jaws of the patient are determined to reproduce the jaw relation will be described.

The jaw-relation reproduction step reproduces a positional relationship between the upper and lower jaws of the patient before the production of dentures. Usually, by using an articulator, the maxillomandibular movement is reproduced on the articulator by adjusting the movement of the condyle path of the articulator and incisal movement in corporation with the movement of the jaws.

It is necessary to decide moving directions that assume masticatory motion and opening/closing movement from the maxillomandibular centric occlusal position.

The conditions of the jaws of the patient include static conditions and dynamic conditions. Typically, the conditions include the position of the centric occlusal position and the directions of protrusive movement and lateral movement, and sometimes the direction of hinge movement.

These occlusal conditions can be reproduced by an occlusion-state reproducing apparatus, typically an articulator. The articulator can reproduce static relations and dynamic relations exactly.

The jaw-relation reproduction conditions include a sagittal condylar inclination, a balancing-side lateral condyle path, a regulatory mechanism of immediate side-shift, and a regulatory mechanism for an angle of lateral condyle path on the working side. Examples of the incisal path regulatory mechanism include a sagittal incisal path inclination and a lateral incisal path guide angle.

The method using the approximate values of the jaw movement in connection with the conditions of the patient is common. For example, the standard condylar distance is 110 mm, the distance between upper and lower arch is 110 mm, the maximum mandibular movement angle is 120 degrees, the inclination of sagittal condylar path is 30 degrees, and the angle of lateral condyle path is 15 degrees.

An important point is that it becomes clear how the upper jaw moves with respect to the lower jaw when the lower jaw is shifted from the centric occlusal position to the lateral movement.

As the simplest method, it is also possible to set the jaws so that the upper jaw slides forward at an angle of 10 degrees from the centric position in parallel to the lower jaw and the upper jaw further slides in the upper direction at an angle of 20 decrees with respect to the occlusal surface from the centric occlusal position.

In recent years, a method for directly reproducing a jaw movement has been investigated and a jaw-movement measurement apparatus has been developed. The jaw movement may be directly acquired by a jaw-movement measurement apparatus so that the jaw movement may be reproduced by a jaw-movement reproducing apparatus.

(2) The pre-grinding denture production step of producing a pre-grinding denture will be described. Here, dentures are produced according to the jaw-relation reproduction conditions of the occlusion-state reproducing apparatus to produce pre-grinding dentures before the step of grinding.

The pre-grinding denture production step is a step of producing dentures according to the maxillomandibular relation obtained in the above occlusion-state reproduction step. In other words, the pre-grinding denture production step is a step of producing a normal denture (steps 6 and 7 in the above denture production process). In the typical process, a wax rim is formed, artificial teeth are arranged along the wax rim and a pre-grinding denture is prepared by a lost wax process. Here, the production method is not particularly limited but the pre-grinding denture can be produced by any typical procedure.

The pre-grinding denture is not ground, so that it cannot be correctly occluded on the occlusion-state reproducing apparatus yet. In order to carry out correct occlusion on the occlusion-state reproducing apparatus, the grinding of the occlusal surface is performed according to the present invention.

(3) The step for measuring denture data with reference points by a denture data measurement apparatus will be described. Here, the denture data measurement apparatus measures the denture data with reference points, comprising three-dimensional image data of the occlusal surface of the denture and reference points representing a positional relation between the occlusion-state reproducing apparatus and the denture.

In this step, the position of the pre-grinding denture in the occlusion-state reproducing apparatus is measured so that an occlusion state can be reproduced in a computer in addition to obtaining the 3D-data of the produced pre-grinding denture. By setting up the maxillomandibular relation of the occlusion-state reproducing apparatus in advance, the occlusion state can be reproduced.

At least three reference points are required for the respective upper and lower arches of the reproducing device. Alternatively, three sides may be used. One side and one point are preferable. Specifically, it may be configured of three needle-like form or spherical surface (preferably globular shape) or may be a combination of a straight side and spherical surface of the reproducing device. Here, the 3D-data is necessary to have reference points for correctly calculating the maxillomandibular relation to be reproduced on a computer. A spherical surface is preferable in order to match the 3D-data on a computer.

Figure 2:
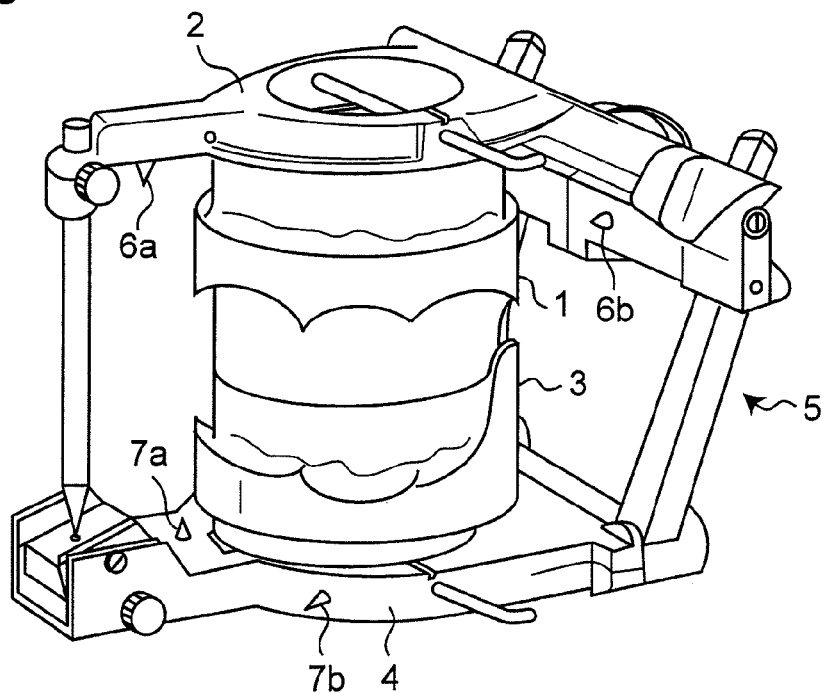
FIG. 2 is a perspective diagram illustrating a state where a maxillomandibular model is attached to an articulator having reference points.

The occlusion-state reproducing apparatus that determines the jaw-relation reproduction condition used for a denture grinding method is an articulator 5 having an upper arch 2 on which an upper jaw model 1 is attached and a lower arch 4 on which a lower jaw model 3 is attached. Preferably, as illustrated in FIG. 2, reference points 6a, 6b, and 6c and reference points 7a, 7b, and 7c are provided on the upper arch 2 and the lower arch 4, respectively.

(4) The occlusion-state reproduction step, which reproduces the occlusion state of the denture data with reference points by using the jaw-relation reproduction conditions, will be described.

In this step, an occlusion state is reproduced on a computer. The maxillomandibular relation of the occlusion-state reproducing apparatus can be arbitrarily configured on the computer.

Here, the positional relationship between the upper and lower jaws can be correctly simulated in the space of the computer. In the computer, the static relationship between the upper jaw and the lower jaw is represented. This relationship includes the reference points which are used for acquiring 3D-data. In the space of the computer, the movements of upper and lower jaws are simulated so that the 3D-data of the upper and lower jaws represents a static relation.

Preferably, the mandibular orthogonal coordinate system of the lower jaw and the orthogonal coordinate system of the upper jaw are configured. To reproduce the maxillomandibular occlusal state, from an arbitrary positional relationship between the upper and lower jaws, a direction along which the orthogonal coordinate system of the upper jaw moves with respect to the orthogonal coordinate system of the lower jaw may be arbitrarily calculated.

Figure 3:
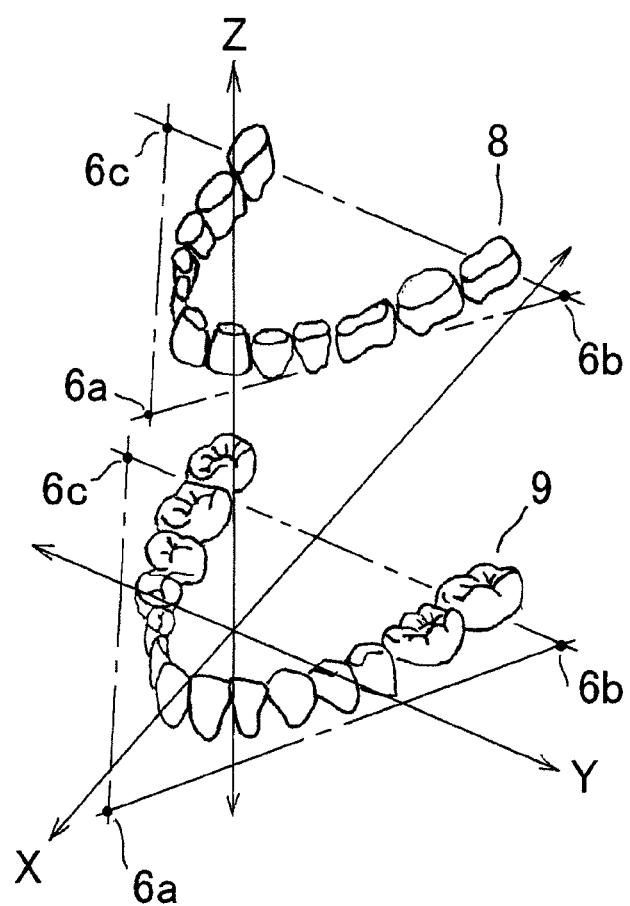
FIG. 3 is a diagram representing three-dimensional data of maxillomandibular occlusal surfaces on a three-dimensional space.

As illustrated in FIG. 3, the reference points on the orthogonal coordinate system of the lower jaw and the reference points on the orthogonal coordinate system of the upper jaw are preferably coincided with the reference points on the computer to reproduce the relationship between the movement of the denture data 8 of the upper jaw and the denture data 9 of the lower jaw.

In each orthogonal coordinate system, the positions of reference points are defined and aligned with the denture data obtained in the step of measuring the denture data.

Figure 4:
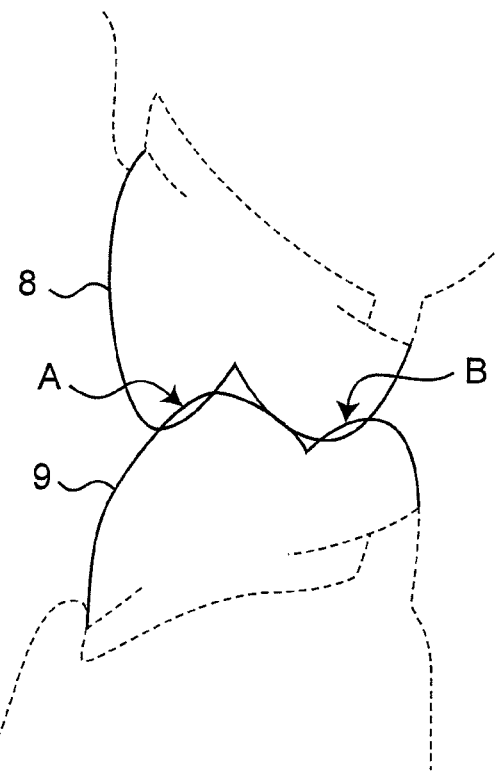
FIG. 4 is a diagram illustrating an occlusion state of the three-dimensional data of the maxillomandibular occlusal surfaces.

As shown in FIG. 4, it can also set up so that an upper jaw orthogonal coordinate system may move to a lower jaw orthogonal coordinate system so that each coordinate axis performs the movement of the denture data 8 of the mandibular denture data 9 represented in the occlusion-state reproduction step.

(5) The determination step for grinding portion, which determines grinding data under static conditions or defined conditions from a portion surrounded by the image of upper and lower jaws from the reproduced occlusion state, will be described.

Here, the region surrounded by the 3D data set in the step of reproducing the occlusion state, that is, as shown in FIG. 4, the region where the occlusion surface of the artificial tooth of the upper jaw and the occlusion surface of the artificial tooth of the lower jaw are overlapped, is observed.

In the case where the region surrounded by the 3D-data is small, the dentures lack in stability. Thus, an overlapped portion of maxillomandibular 3D-data is adjusted by the hinge movement of maxillary 3D-data or movement thereof in the direction of lowering an occlusal vertical dimension. If the overlapped portion of the 3D-data is large, there is no cusp of the tooth due to a large number of cuttings. Thus, an overlapped portion of maxillomandibular 3D-data is adjusted by the hinge movement of maxillary 3D-data or movement thereof in the direction of increasing the occlusal vertical dimension. The hinge movement or the shift in occlusal vertical dimension may be used in arbitrarily combination.

Figure 5A:
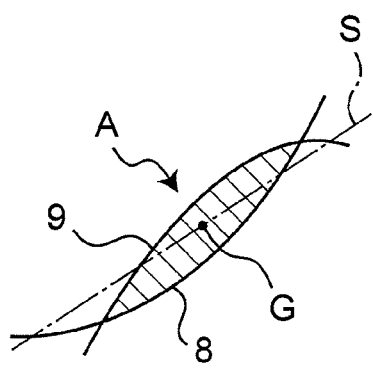
FIG. 5A is a diagram illustrating a portion surrounded by the three-dimensional data of the maxillomandibular occlusal surfaces.

Next, as illustrated in FIG. 5A, a grinding surface is determined by moving the maxillary 3D-data 8 or the mandibular 3D-data 9 so that the 3D-data overlapped portion A is frictionally moved during the movement of the upper and lower jaws. It is performed by cutting each 3D-data overlapped portion along the arbitrary defined grinding surface S at the time of forward movement, back movement, or lateral movement from the centric occlusal position.

Figure 5B:
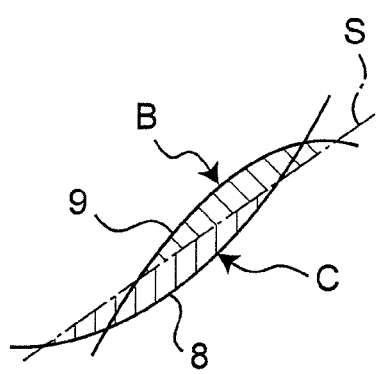
FIG. 5B is a diagram illustrating a grinding portion of the maxillomandibular occlusal surfaces.

Although the grinding surface S may not pass through the maxillomandibular 3D-data overlapped portion, preferably, it may pass through the overlapped portion between the maxillary 3D-data 8 and the mandibular 3D-data 9. As illustrated in FIG. 5B, cuspal portions B and C surrounded by the surface extended from the grinding surface S in the overlapped portion between 3D-data 8 and 9 are provided as cutting portions, respectively. These portions are referred to as grinding portions and the data thereof is referred to as grinding data.

The arbitrary defined grinding surface S is a surface extending in the direction of a forward movement, a backward movement, or a lateral movement and the angle of each surface is arbitrary defined with respect to an occlusal plane. It is preferable that the angle of the grinding surface S is set to 5 to 60 degrees with respect to the occlusal plane. An angle of a surface where the cusp of tooth touches is preferably 5 to 45 degrees in the forward or backward direction and 20 to 60 degrees in the lateral movement.

The movement direction is a direction along which the maxillary orthogonal coordinate system moves with respect to the mandibular orthogonal coordinate system at an arbitrary point within the range surrounded by the maxillary 3D-data and the mandibular 3D-data in the dynamic relation represented by the occlusion-state reproduction step. The movement direction is preferably linear. Alternatively, the movement direction may be curved. The movement direction may be approximate to a straight line. Alternatively, a curved line may be applied to the movement direction. In other words, the movement direction is a straight line or a curved surface. Preferably, it is a straight line or cylindrical surface.

Furthermore, the arbitrary point in range A surrounded by the maxillary 3D-data 8 and mandibular 3D-data 9 is the center of gravity G of the range surrounded by maxillary 3D-data 8 and the mandibular 3D-data 9.

When the range surrounded by the maxillary 3D-data 8 and the mandibular 3D-data 9 is represented by n points on the space, the center of gravity G is preferably calculated as $X'$, $Y'$, $Z'$ obtained by converting X, Y, and Z axis of a mandibular orthogonal coordinate system and X, Y, and Z axis of a maxillary orthogonal coordinate system XYZ axis into those of the same orthogonal coordinate system, respectively, and dividing the sums of the values of the respective axes X, Y, and Z are divided by n. The grinding surface S is a plane including the movement direction of the upper jaw with respect to the lower jaw that passes through the values of $X'$, $Y'$, and $Z'$.

This movement direction is calculated by the reproduction method represented in the occlusion-state reproduction step. When the movement direction is reproduced by the articulator, these adjustment mechanisms can be reproduced on the computer in the case of an arcon type articulator or a condylar type articulator. The arcon type articulator is preferable.

The condylar distance of the articulator is 50 to 170 mm, preferably 80 to 140 mm, more preferably 100 to 120 mm. It is preferred to have an average condylar distance as a fixed value of 110 mm. A distance between the upper arch and the lower arch is about 80 to 120 mm. Any distance between the upper arch and the lower arch is allowable as long as it is determined where appropriate.

The condylar distance and the distance between the upper arch and the lower arch are calculated from numerical values previously defined by the condyle path regulatory mechanism and the incisal patch regulatory mechanism, which specify the maxillomandibular movement of the articulator.

Specifically, examples of the condyle path regulatory mechanism include an inclination of sagittal condylar path, a balancing-side lateral condyle path, a regulatory mechanism for immediate side-shift, and a regulatory mechanism for an angle of lateral condyle path on the working side. Examples of the incisal path regulatory mechanism include a sagittal incisal path inclination and a lateral incisal path guide angle.

An inclination of sagittal condylar path is −30 degrees to +90 degrees, preferably −0 degree to +50 degrees, more preferably −20 degrees to +80 degrees.

A balancing-side lateral condyle path is 0 degrees to +40 degrees, preferably +10 degrees to +20 degrees, more preferably 0 degree to +30 degrees.

A regulatory mechanism for immediate side-shift is 0 to 5 mm, preferably 0 to 8 mm, more preferably 0 to 10 mm.

A regulatory mechanism for an angle of lateral condyle path on the working side is −50 degrees to +60 degrees, preferably −40 degrees to +50 degrees, more preferably −30 degrees to +30 degrees.

A sagittal incisal path inclination is −30 degrees to +90 degrees, preferably −20 degrees to +80 degrees, more preferably −10 degrees to +75 degrees.

A lateral incisal path guide angle is −0 degree to +90 degrees, preferably −0 degrees to +50 degrees.

The maxillary orthogonal coordinate system is calculated with respect to the mandibular orthogonal coordinate system, which can move in accordance with these regulation mechanisms.

From the names or the like of commercial articulators, settings which can appropriately select only adjustment items are preferable. In the case where an unadjustable articulator is used, it is preferable that the fixed values of the articulator are fixedly entered without change when the name of this articulator is selected. The defined conditions are conditions being set to remove protruded portions to prevent upper and lower jaws from being caught while allowing them smoothly rubbing with each other.

The grinding data obtained in the present step is used as CAD data for grinding dentures. An NC program for processing in the grinding step for pre-grinding dentures is prepared. A computer numerical control (CNC), which controls a moving distance, a moving speed, and so on of tools in machine work by a computer, is used for grinding dentures. This process is referred to as CAM.

Figure 6:
FIG. 6 is a diagram illustrating a grinding portion of the occlusal surface.

FIG. 6 is a diagram illustrating faces to be ground in occlusal surfaces. Grinding is performed substantially in a bilaterally-symmetric manner. Thus, lead lines 1, 2, and 3 represent only one of jaws, respectively. When the upper and lower jaws are occluded, occlusal facets, where the upper and lower jaws make contact with each other, come into surface contact with the corresponding ones. Thus, the occlusal facets become surfaces being rubbed in accordance with the movement of the jaws.

Lead line 1 denotes posterior occlusal facets, lead line 2 denotes protrusive occlusal facets, and lead line 3 denotes balancing occlusal facets.

In other words, in the figure, reference numeral 1 denotes each of the surface portions to be ground at a certain angle, 2 denotes each of the surface portions to be ground at another angle, and 3 denotes the surface portions to be ground at a still another angle. However, these surfaces represented by these reference numerals are illustrative only. When considering occlusal static or dynamic relation, it is preferable to adjust or calculate the angles of the respective surfaces so that the surfaces are rubbed with the corresponding surfaces in their correct directions. Alternatively, however, these surface portions may be those to be ground almost at the same angle.

(6) The preparation step for denture data with reference points having grinding data, in which the denture data with reference points having grinding data, where denture data with reference points is additionally provided with grinding data, is prepared, will be described.

The grinding surface, which is the above grinding data, is aligned with the denture data with reference points to determine a grinding portion, thereby obtaining denture data reference points having grinding data. Here, based on the reference points, an important point is that a portion which should not be ground and a portion which should be ground are defined based on the reference points.

Therefore, by overlapping the indication parts of the reference points that represents a positional relationship between dentures and the reference point portions of the denture data with reference points having grinding data together, grinding portions of the dentures can be determined.

(7) A grinding step for pre-grinding dentures, which grinds a pre-grinding denture based on the denture data with reference points having grinding data, will be described.

Grinding data is used as CAD data and create an NC program for processing in this step. This is a program of a computer numerical control (CNC) which controls a moving distance, a moving speed, and so on tools in machine work by a computer. Grinding of dentures is performed using this program.

Figure 7:
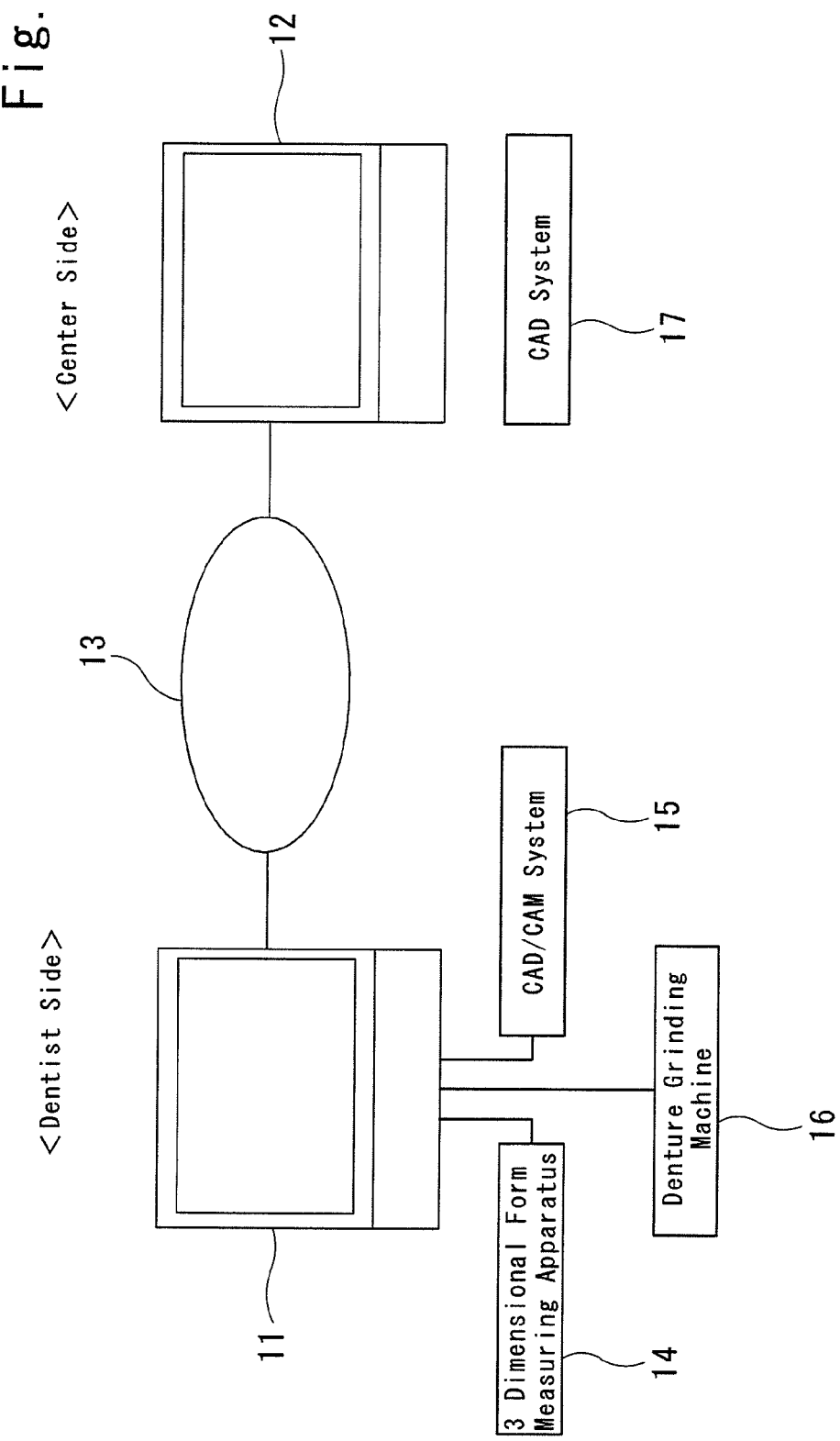
FIG. 7 is a block diagram illustrating an occlusal adjustment system.

FIG. 7 is a schematic diagram illustrating the configuration of a denture occlusal adjustment system according to an embodiment of the present invention.

A personal computer (hereinafter, simply referred to as a computer) 11 on a dentist side can be connected to a personal computer (hereinafter simply referred to as a computer) 12 on a data center side of a grinding-data provider through Internet 13. The dentist side prepares patient's dentures. The center side is a vendor (provider) who offers cutting data of an occlusal adjustment portion in accordance with occlusal-surface shape data and occlusal-surface data from the dentist side.

On the dentist side, the computer 11 is connected to a three-dimensional form measuring apparatus 14, a CAD/CAM system 15, and a denture grinding machine 16. The CAD/CAM system 15 creates a NC program for occlusal adjustment and grinding based on shape data created by CAD. The denture grinding machine 16 cuts a denture according to the NC program, and performs occlusal adjustment and grinding. On the center side, the computer 12 is connected to the CAD system 17.

First Embodiment

Figure 8:
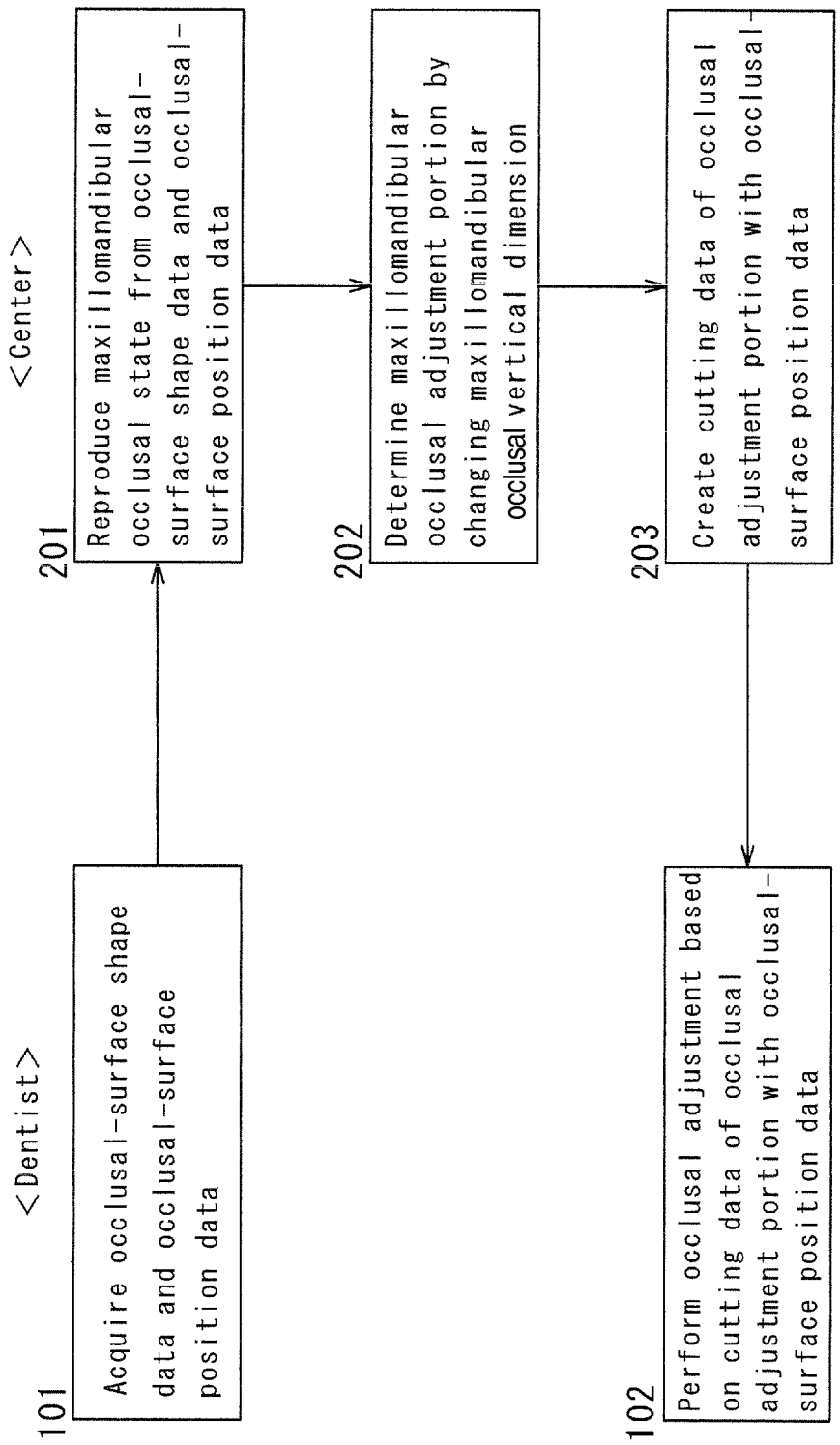
FIG. 8 is a flow chart illustrating operations on a dentist side and operations on a center side according to a first embodiment.

FIG. 8 illustrates the operation of an occlusal adjustment system according to a first embodiment. On the dentist side, the occlusal surface of artificial tooth is measured by the three-dimensional form measuring apparatus at the time of occlusal adjustment (step 8) after arranging front tooth and molar tooth on a wax rim in the denture-production step described above. The measurement results are incorporated into the computer. Then, the CAD/CAM system acquires occlusal-surface shape data and occlusal-surface position data.

The term "occlusal-surface shape data" means data that represents the shape of an occlusal surface. Preferably, an occlusal view emerges from the occlusal surface direction. More preferably, the slope of the pharynx direction is important to the upper jaw. The slope of the pharynx direction is important to the maxilla, and the slope of the labial surface direction is important to the lower jaw. Thus, it is preferable that the data represents data in this direction in great detail. Specifically, a method for acquiring data for the upper jaw in the pharynx direction and the lower jaw in the labial surface direction is desirable when data is obtained.

The term "occlusal-surface position data" means data that represents a position of occlusal-surface shape data in the buccal cavity. Alternatively, because of representing the positional data of the occlusal-surface shape data in the buccal cavity, it may be one representing the relationship between the occlusal-surface shape data and the occlusal-state reproducing apparatus (articulator). As long as a relationship between an articulator and a plaster model, which are used in the denture production, is represented, the data of denture base may be used. As long as a method for occlusal adjustment of dentures ground in a manner similar to the present method, it is preferable to represent a positional relationship with a reference point representing a positional relationship with grinding data.

Figure 15:
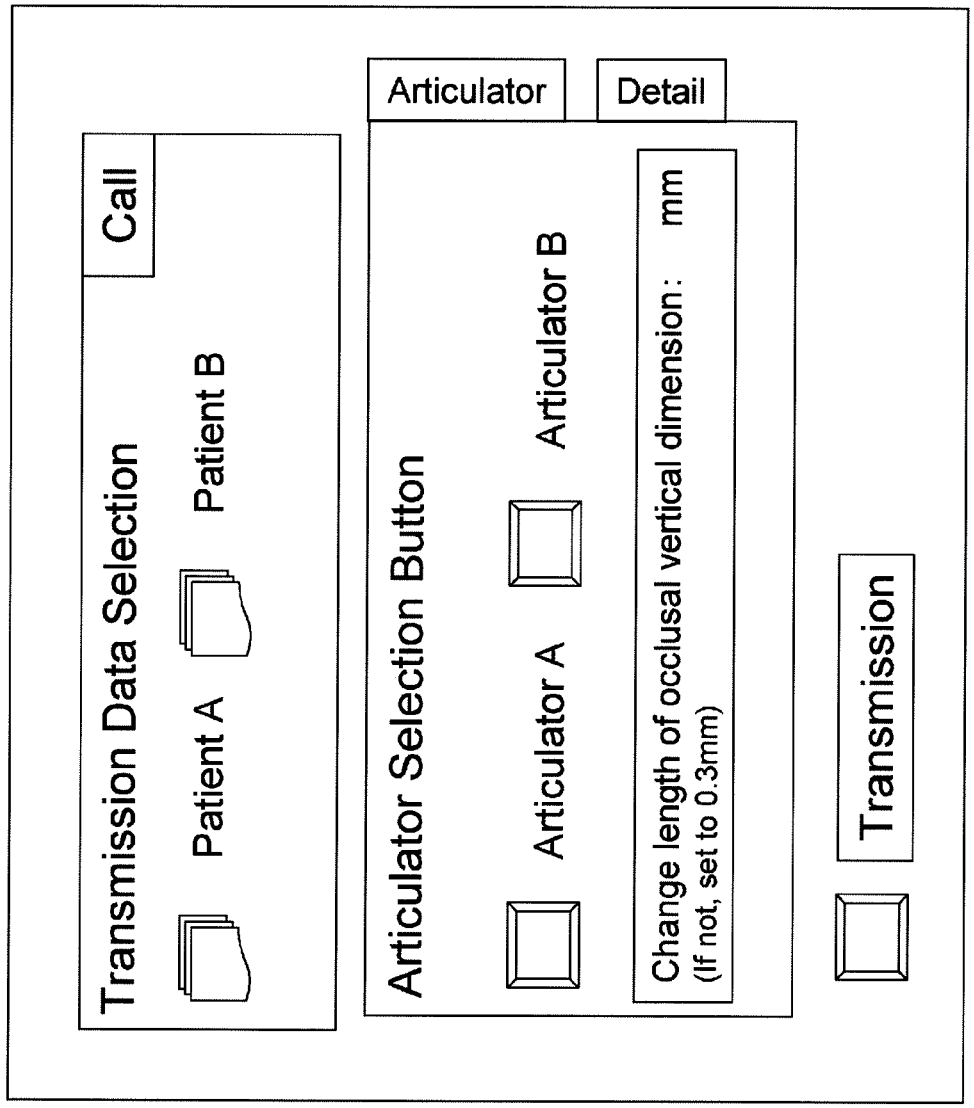
FIG. 15 is a diagram illustrating a state where an articulator is selected in a data-transmission screen on a dentist side.

FIG. 15 illustrates a data-transmission screen of a computer on the dentist side.

The data-transmission screen includes a transmission-data selection portion, an articulator selection button, and a transmission button.

When a call of the transmission-data selection portion is clicked, a holder that stores occlusal-surface shape data and occlusal-surface position data for every patient is displayed.

When a "articulator" tab in the articulator selection portion is clicked, as illustrated in FIG. 15, a button for articulator A and a button for articulator B are displayed and each of them can be selected. In addition, a changed length of occlusal vertical dimension can be input. If it is not stated, the change length of occlusal vertical dimension is set to 0.3 mm.

Figure 16:
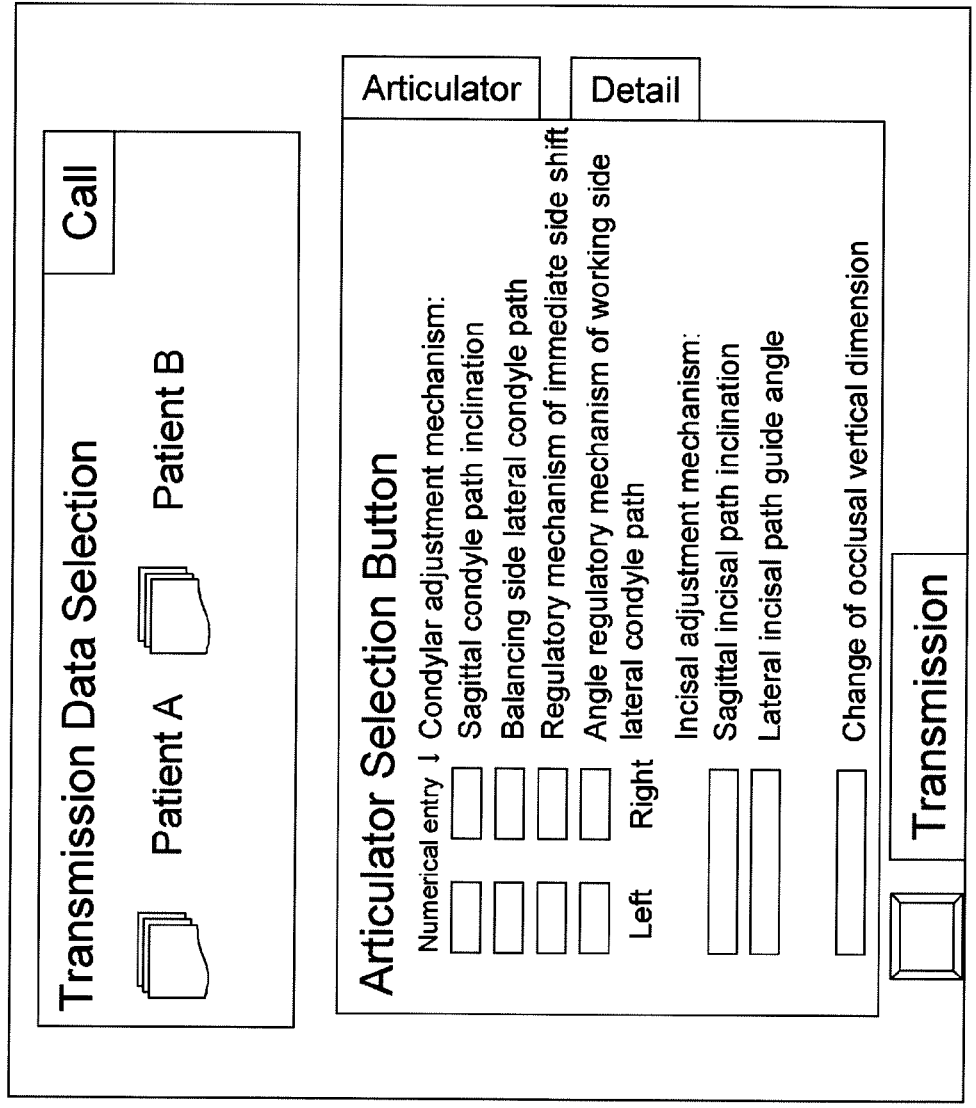
FIG. 16 is a diagram illustrating a state where detail is selected in a data-transmission screen on a dentist side.

When a tab "detail" is clicked, as illustrated in FIG. 16, an input screen of setting data of the articulator is displayed. Thus, setting values (sagittal condyle path inclination, balancing side lateral condyle path, regulatory mechanism of immediate side shift, and angle regulatory mechanism of working side lateral condyle path in condyle adjustment mechanism; sagittal incisal path inclination and lateral incisal path guide angle in the incisal path regulatory mechanism; change of occlusal vertical dimension) of the articulator can be input.

One of displayed holders of patient A and patient B is selected. When a standard articulator is available, either articulator A or articulator B is selected. Then, a changed length of occlusal vertical dimension is input as needed. When the standard articulator is not available, detailed numerical values are input. Then, the data is transmitted to the center side when a transmission button is placed.

The acquired occlusal-surface shape data and occlusal-surface position data are transmitted from the computer of the dentist side to the computer on the center side through the Internet.

On the center side, from the occlusal-surface shape data and the occlusal-surface position data received from the dentist side, a maxillomandibular occlusal state is reproduced and a maxillomandibular occlusal adjustment portion is determined by a CAD system.

Here, from the occlusal-surface position data, a portion to be subjected to an occlusal adjustment is determined by using jaw movement data. Jaw-movement data uses the set data of the articulator which can follow the articulator in a simple manner.

In addition, a standard jaw movement and the position of an occlusal plane are assumed, and maxillomandibular occlusal adjustment portion is determined by changing a maxillomandibular occlusal vertical dimension.

When the occlusal-surface position data are reference points of the articulator, based on individual identification information of a patient (such as ID, medical chart No., address/name, and file No.), the data in the form of jaw-movement data of the patient (such as jaw-movement data, articulator setting data, and articulator movement data, preferably articulator setting data) for every patient and the reference points are used for determining a maxillomandibular occlusal adjustment portion.

It is preferred to acquire the setting conditions (condylar distance, distance between upper arch and the lower arch, sagittal condylar path inclination, balancing-side lateral condyle path angle, immediate side-shift, angle of working side lateral condyle path, working side sagittal incisal path inclination, and lateral incisal path guide angle) of an articulator from the dentist side are preferably acquired.

After determining a maxillomandibular occlusal adjustment portion, the cutting data including data of the occlusal adjustment portion and occlusal-surface position data is created by a CAD system. The cutting data is transmitted to the dentist side from the center side by the computer.

Figure 19:
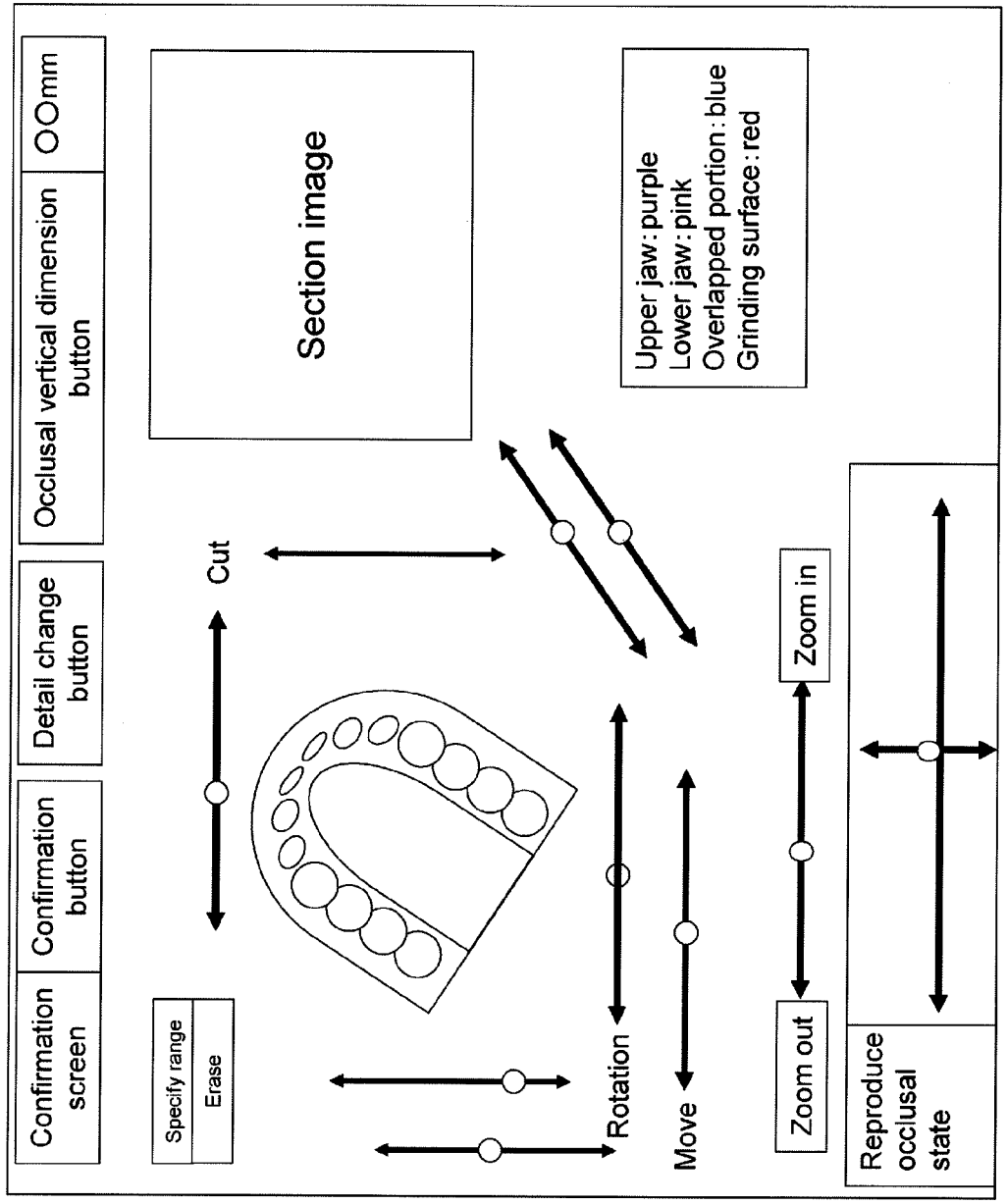
FIG. 19 is a diagram illustrating a confirmation screen on the dentist side.
Figure 20:
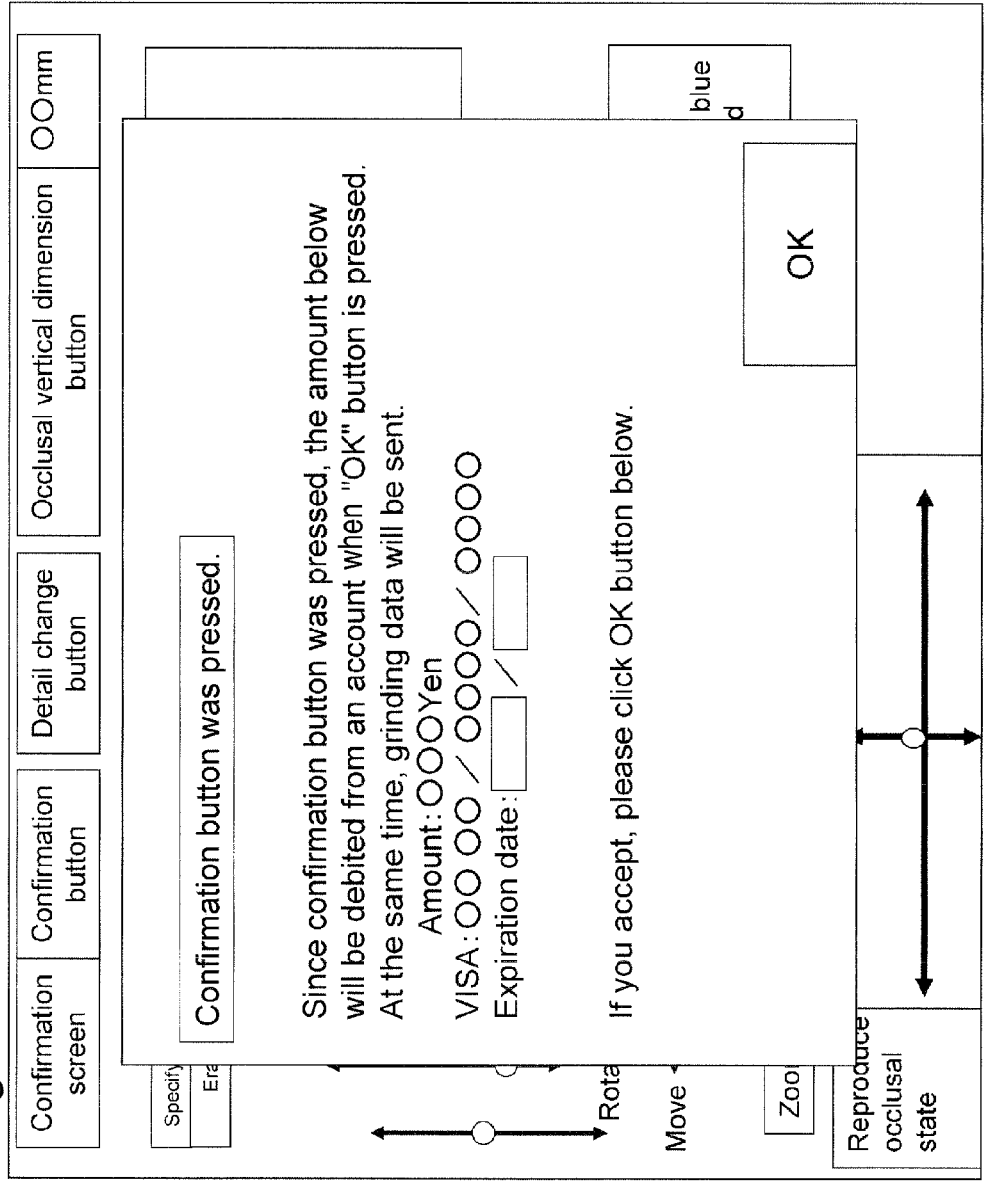
FIG. 20 is a diagram illustrating the confirmation screen on the dentist side, where a charging message is displayed.

As illustrated in FIG. 19, the display side of the computer on the dentist side displays a fact that cutting data is received. When an OK button is pressed, as illustrated in FIG. 20, a holder storing the cutting data (CAM data) is formed at a low rank of the data holder of patient A in the transmission screen.

On the dentist side, based on the cutting data received from the center side, a denture is cut by a grinding machine and then subjected to an occlusal adjustment.

Second Embodiment

Figure 9:
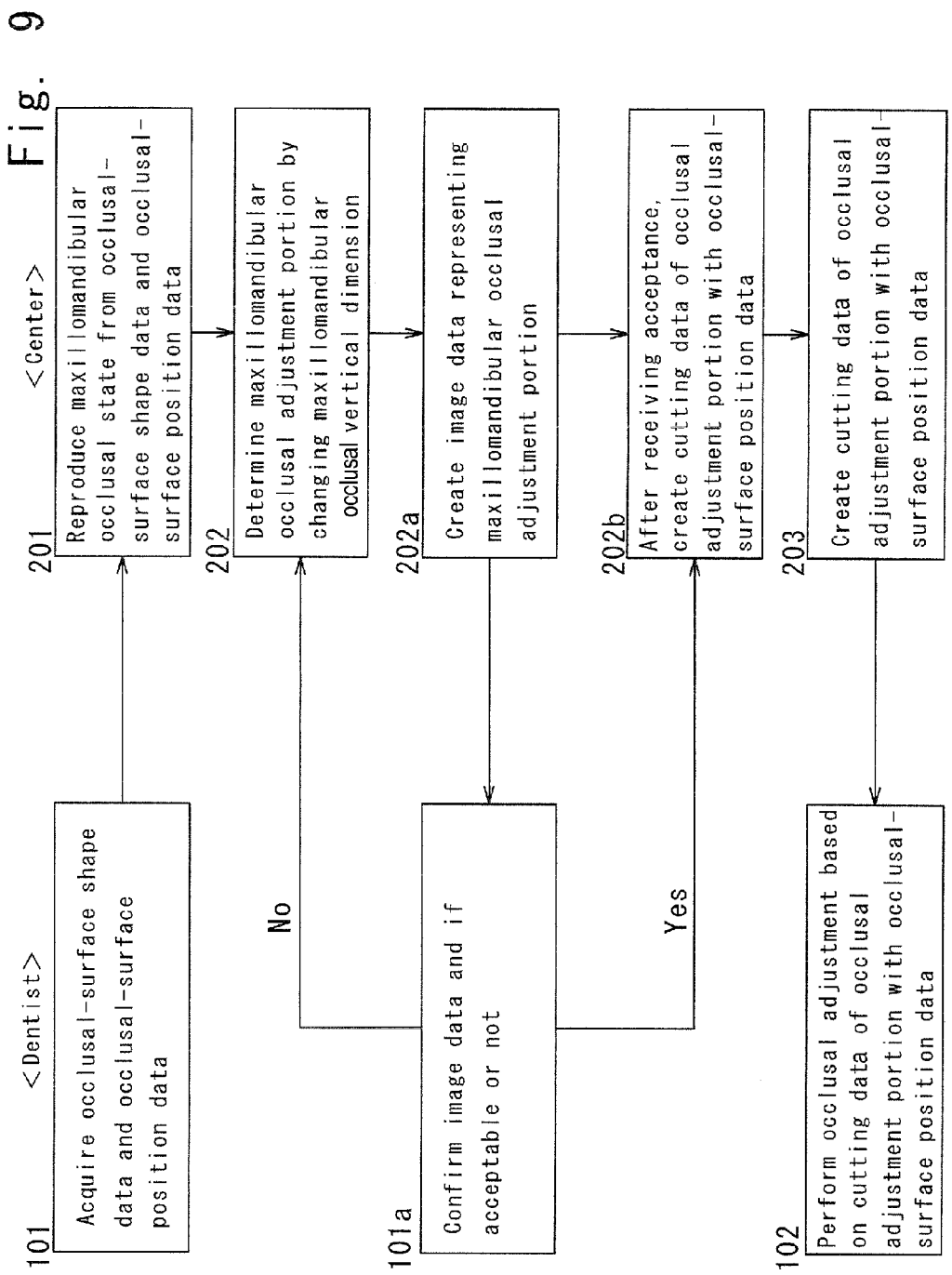
FIG. 9 is a flow chart illustrating operations on a dentist side and a center side according to a second embodiment.

FIG. 9 illustrates operations of an occlusal adjustment system according to a second embodiment. In this second embodiment, a step for allowing the dentist side to confirm an occlusal adjustment portion in advance after determination of the occlusal adjustment portion in the first embodiment.

That is, image data representing an occlusal adjustment portion is created by a CAD system. Then, the image data is transmitted to the dentist side from the computer.

It is preferable that data to be subjected to an occlusal adjustment is found in the image data. It is preferable that the occlusal adjustment portion is classified by color in the occlusal surface. The amount of deletion is preferably represented in terms of volume.

It is preferable that the final image data is simultaneously given with work data obtained at the time of occlusal adjustment.

It is preferable to save the occlusal-surface shape data for every patient in chronological order.

FIG. 19 illustrates a confirmation screen of data sent from the center side to the dentist side. In the left side of the middle of the image, image data representing an occlusal adjustment portion is displayed. Around the image data, slide levers are displayed for performing cut, rotation, movement, and zoom in/out of an image by using a mouse. A range specification button that specifies the range of an image and an eraser button that can eliminate the arbitrary portions of an image are displayed on the upper left of image data. Under the image data, a slide lever is provided for moving the upper jaw and the lower jaw right-and-left and forward-and-backward and reproducing an occlusal state. On the right of the image data, a cross-sectional image of a portion cut by a cut slide lever is displayed. Under the cross-sectional image, a color-changing portion is provided for changing colors of upper jaw, low jaw, overlapped portion, and grinding portion.

Upper part of the screen is provided with a confirmation button, a detail change button, an occlusal vertical dimension change button, and an occlusal vertical dimension numerical value input portion.

The confirmation button is pressed when accepting image data.

The detail change button is pressed when image data is not accepted and the screen is desired to return to the articulator detailed screen so that the numerical value of the articulator can changed.

The occlusal vertical dimension change button is pressed when the image data is not accepted and an occlusal vertical dimension is desired to be changed.

The occlusal vertical dimension numerical value input portion can input the numerical value of an occlusal vertical dimension when the occlusal vertical dimension change button is pressed.

The dentist side confirms image data received from the center side. A signal of acceptable or unacceptable is transmitted by the computer.

On the center side, when the signal of unacceptable is received, the maxillomandibular occlusal vertical dimension is further changed to determine a maxillomandibular occlusal adjustment portion. Then, the image data is transmitted until an acceptance is obtained. When the signal of acceptable is received, cutting data including occlusal-surface position data and occlusal-adjustment portion data is created. As described above, cutting data is transmitted from the center side to the dentist side by the computer.

Third Embodiment

Figure 10:
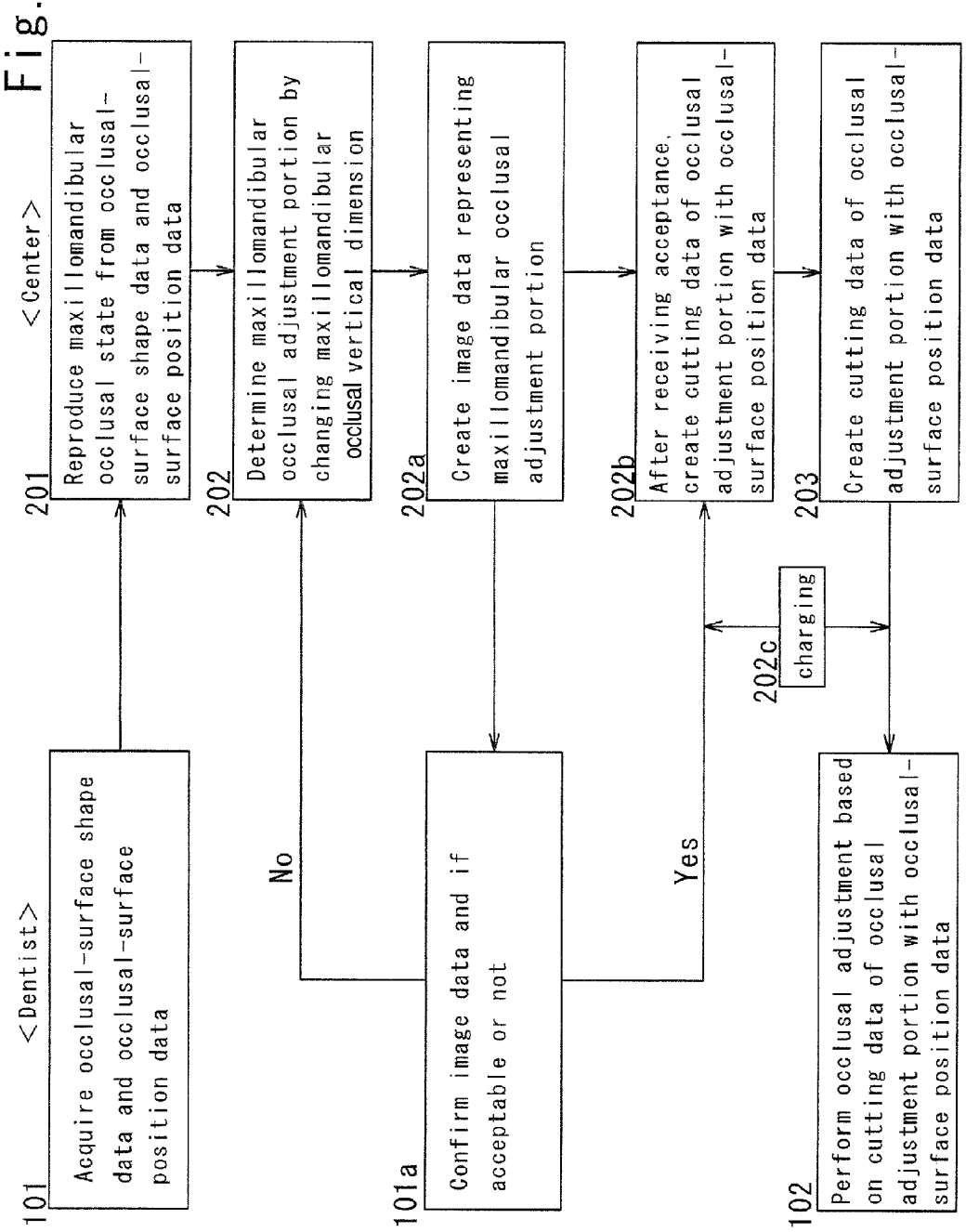
FIG. 10 is a flow chart illustrating operations on a dentist side and a center side according to a third embodiment.

FIG. 10 illustrates operations of an occlusal adjustment system according to a third embodiment. In the third embodiment, when the dentist accepts image data of an occlusal adjustment portion, charging for offering the image data on the center side is made. FIG. 20 illustrates an example in which data screen sent from the center side to the dentist side notifies that the confirmation button is pressed, it is charged when an OK button is pressed, and also notifies the amount of charging and a charging method. The charging may be performed when the center side offers cutting data.

Fourth Embodiment

Figure 11:
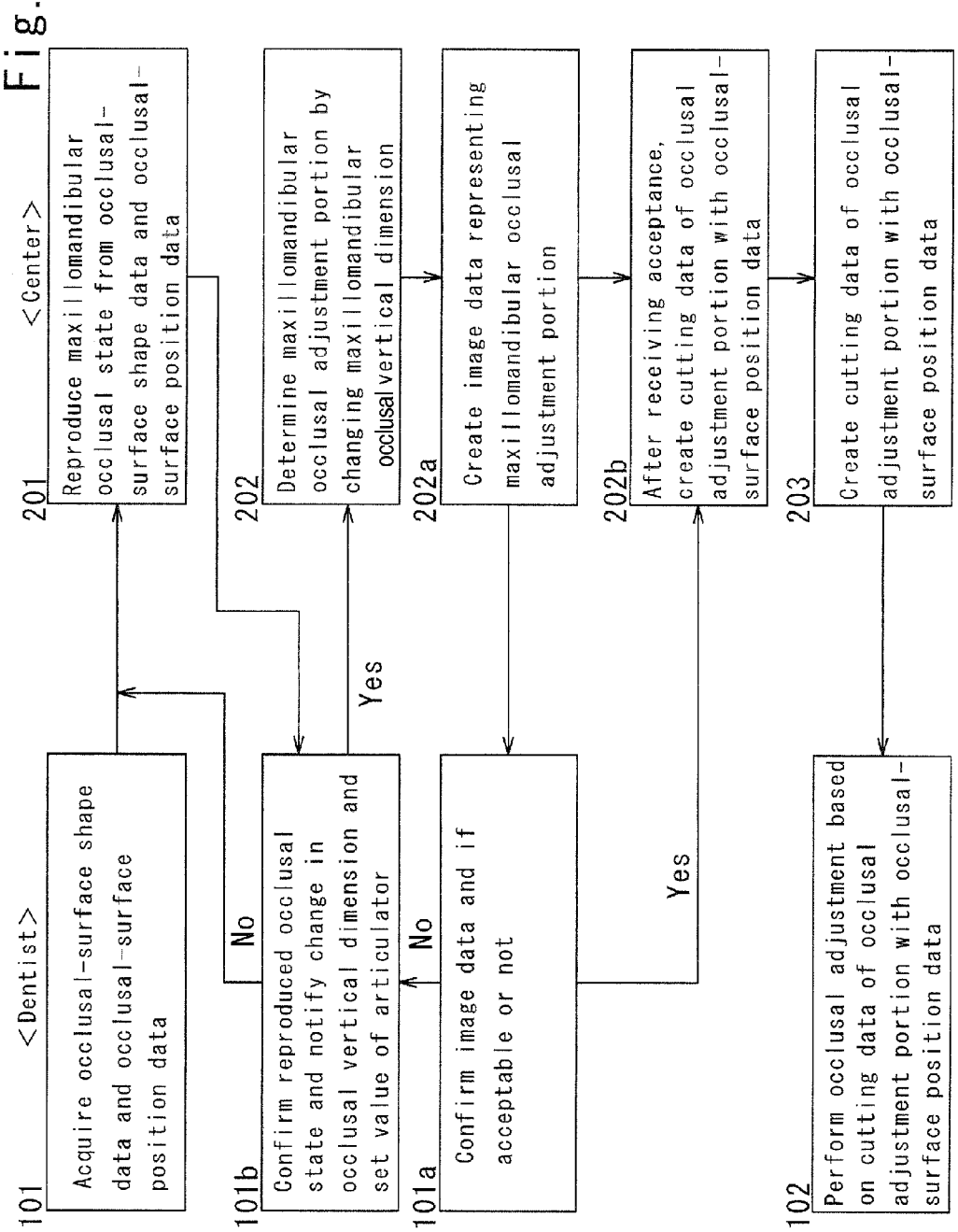
FIG. 11 is a flow chart illustrating operations on a dentist side and a center side according to a fourth embodiment.
Figure 21:
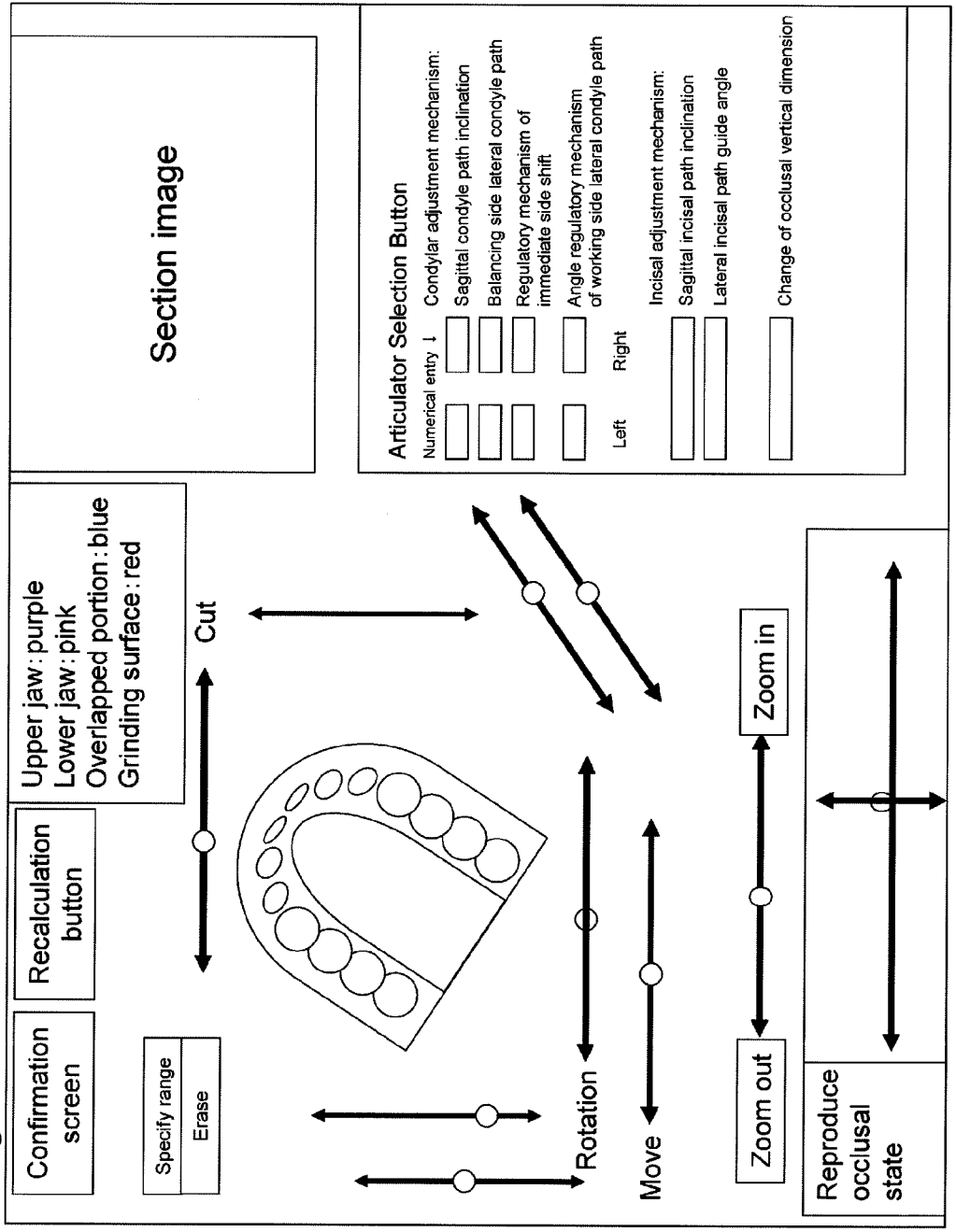
FIG. 21 is a diagram illustrating an input portion for changing an occlusal vertical dimension and set values of an articulator and a re-calculation button on the confirmation screen on the dentist side.

FIG. 11 illustrates operations of an occlusal adjustment system according to a fourth embodiment. In this fourth embodiment, when the dentist side does not accept image data, a change in occlusal vertical dimension and a change in set value of an articulator are notified. As illustrated in FIG. 21, on the confirmation screen, the values of an occlusal vertical dimension and the set value of the articulator are changed. When a re-calculation button is placed, the occlusal vertical dimension and the set value of the articulator are sent to the center side.

On the other hand, when the notice of changes in occlusal vertical dimension and set value of the articulator is received from the dentist side, the center side determines the maxillomandibular occlusal adjustment portion at the changed occlusal vertical dimension set value and the changed set value of articulator, and it transmits image data until acceptance is acquired.

Fifth Embodiment

Next, a method for reducing a slight displacement in a buccal cavity at the final stage of the denture production will be described.
In the denture production,
1. rims of the upper and lower jaws are molded using silicone models;
2. temporary wax denture is produced;
3. the relationship between the upper and raw jaws is acquired while being attached in a buccal cavity;
4. a maxillomandibular movement is reproduced by an articulator; and
5. a wax rim is replaced with resin after the arrangement of artificial teeth.

The above procedures are the same as those generally performed. Pre-grinding dentures being prepared are returned into the buccal cavity of a patient and then the positional relationship between the upper and lower jaws is confirmed again. By moving the jaws of the patient attached with dentures, a feel is confirmed and the positions of the upper and lower jaws are reconfirmed. In this case, the dentures may be slightly displaced compared with one initially attached and confirmed in early stages (the above 3). It may be caused by the following reasons: The initial wax rims are not in the form of dentures and a patient feels uncomfortable because of difficulty in usual maxillomandibular movement.

In the fifth embodiment, impressions in occlusion of the upper and lower jaws are used as data to be transmitted from the dentist side to the center side without the use of occlusal-surface shape data and occlusal-surface position data as described in the first to fourth embodiment.

Therefore, first, maxillary denture and mandibular denture are attached to a patient and then tapped or the like to reduce uncomfortable feeling. Subsequently, a tray with poured wax or silicone is placed between the upper and lower jaws of a patient. Then, the patient slowly bites the tray.

Figure 22A:
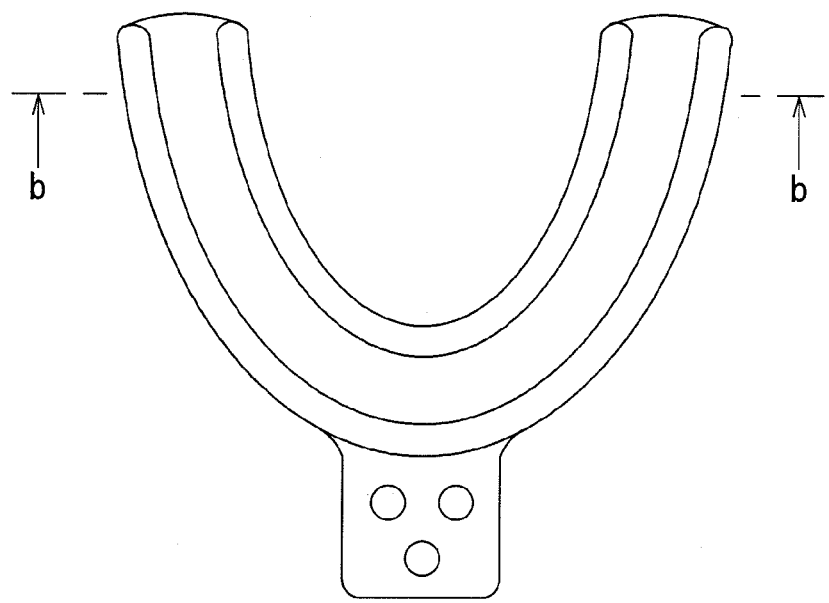
FIG. 22A is a plan view of a tray for acquiring a maxillo-mandibular occlusal surface with wax or silicone.
Figure 22B:
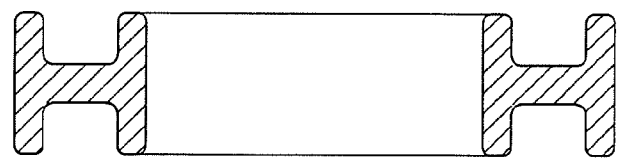
FIG. 22B is a cross-sectional diagram along a b-b line in FIG. 22A.

The tray may be in the form of one illustrated in FIG. 22, so that the shapes of the upper and lower occlusal surfaces can be obtained. The tray is designed so that wax or silicone can be placed on the upper and lower sides.

The tray is gently taken out from the inside of the buccal cavity after waiting hardening of wax or silicone. The taken-out impression represents a correct positional relationship of a patient between the upper and lower jaws. Then, the positional relationship between the upper and lower jaws is read by a three-dimensional shape measuring apparatus (3D scanner).

The 3D scanner needs to acquire the upper and lower jaws relationship clearly. When a reference point is placed in the tray, the maxillomandibular relationship can be read correctly. The configuration of the reference point is not specifically limited. However, it is important that the reference point can be read by a double scanner at the time of obtaining a maxillomandibular occlusal surface. Preferably, for example, the reference point may be three projected spheres which can be read from a double scanner at the time of obtaining maxillomandibular occlusal surface.

Figure 12:
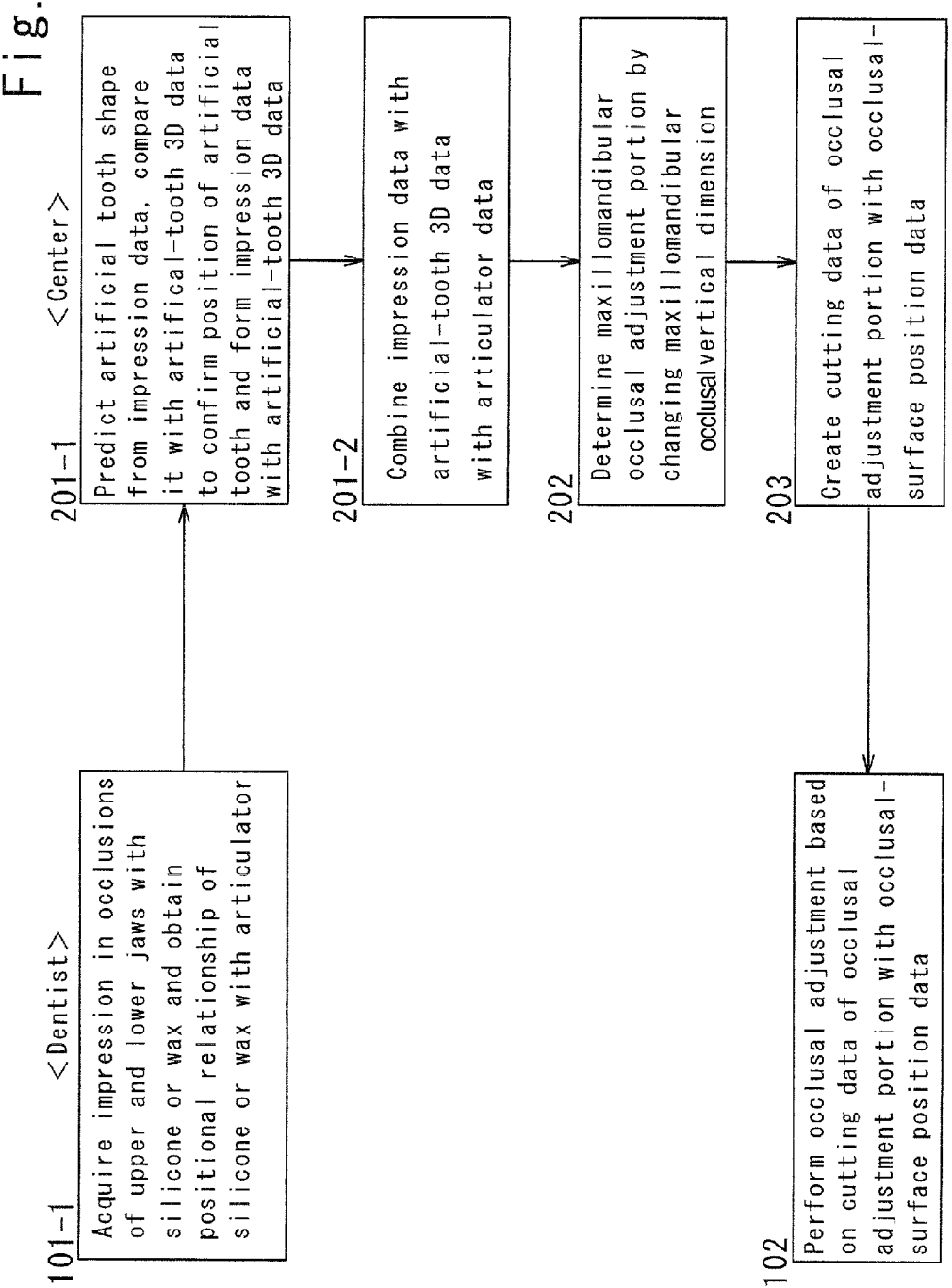
FIG. 12 is a flow chart illustrating operations on a dentist side and a center side according to a fifth embodiment.

FIG. 12 illustrates operations of an occlusal adjustment system according to a fifth embodiment. The 3D dimensional data of acquired impressions (impression data) is transmitted from the computer on the dentist side to the computer on the center side through the Internet.

On the center side, a maxillomandibular occlusal state is reproduced by a CAD system according to the impression data received from the dentist side. Then the maxillomandibular occlusal adjustment portion is determined.

It is also preferable that an artificial tooth shape is predicted from the impression data and then compared with artificial-tooth 3D data which is previously held to confirm the position of artificial tooth in the pre-grinding denture, and form impression data with artificial tooth 3D data.

When the form of the occlusal surface is obtained, the shape of the occlusal surface is read and reversed by the 3D scanner and can be directly used as occlusal form.

When providing impression in wax, the number of cusps and an impression of the shape of a wax are acquired. The shape data of the artificial tooth used in advance are held.

The impression of the held artificial tooth-shape data is compared with that of wax in advance.

Instead of the tray where the wax or silicone is poured, there is a method for measuring a contact position of the opposing teeth with reference to the impressions remained by contact of the opposing teeth on the wax-coated occlusal surface. Alternatively, there is another method for applying wax to an occlusal surface, contacting opposing teeth with each other, and determining a relationship between upper and lower jaws from an image of front teeth portion or a 3D-image thereof of a patient.

Then, a method for determining an occlusal adjustment portion and a subsequent method can be described by direct application of any of the embodiments 1 to 4. Thus, the description will be omitted.

Sixth Embodiment

According to a sixth embodiment, an occlusal adjustment system is configured to perform grinding with CAD/CAM until it is accepted when correct grinding is performed or not after grinding with CAD/CAM.

This method is carried out as a therapeutic intervention in clinical, and needs the confirmation of the medical treatment by a dentist.

Figure 13:
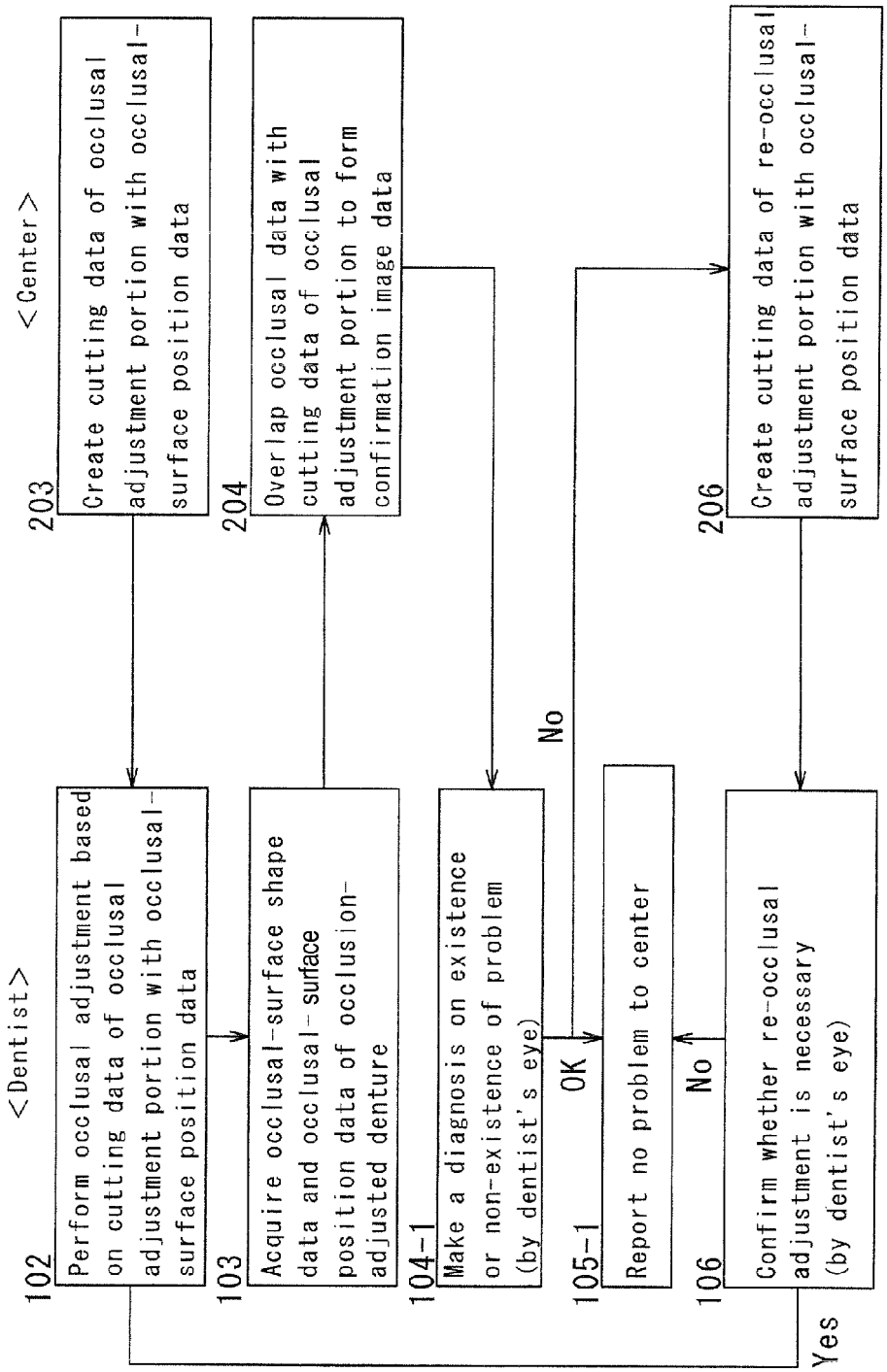
FIG. 13 is a flow chart illustrating operations on a dentist side and a center side according to a sixth embodiment.

FIG. 13 illustrates an occlusal adjustment confirmation operation according to a sixth embodiment.

Figure 23:
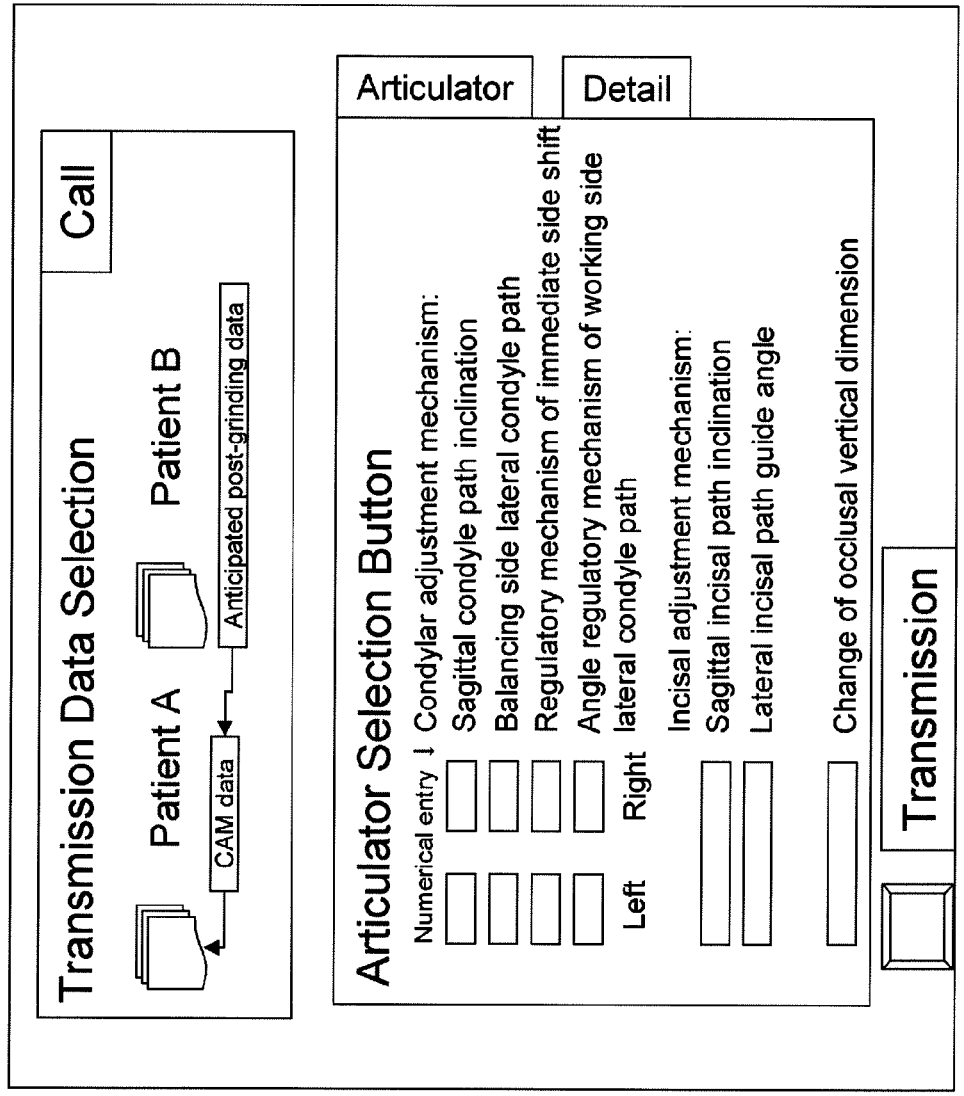
FIG. 23 is a diagram illustrating a data-transmission screen on the dentist side, where a state of forming a holder of anticipated post-grinding data is represented.

In this embodiment, when the center side transmits cutting data of an occlusal adjustment portion with occlusal-surface position data, anticipated post-grinding data is transmitted with CAM data. Thereby, as shown in FIG. 23, the holder of CAM data and anticipated post-grinding data is created at the low rank of the data holder of patient A in a transmitting screen.

First, the occlusal-surface shape data and occlusal-surface position data of occlusion-adjusted dentures are acquired in the dentist side. The manner of data acquisition here is the same as those of the first embodiment.

Figure 24:
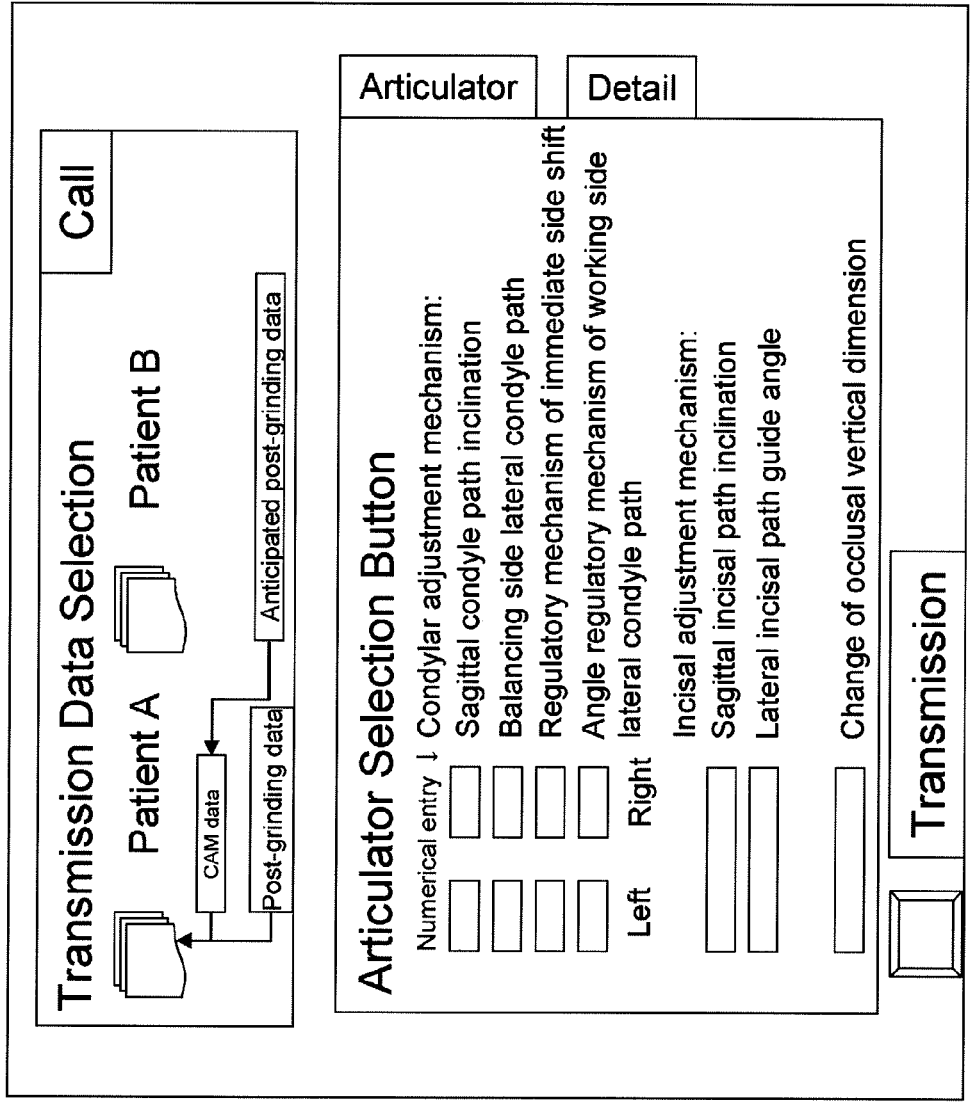
FIG. 24 is a diagram illustrating a data-transmission screen on the dentist side, where a state of forming a holder of post-grinding data is represented.

Post-grinding data acquired from the occlusion-adjusted dentures is transmitted from the dentist to the center together with anticipated post-grinding data, as illustrated in FIG. 24.

Figure 25:
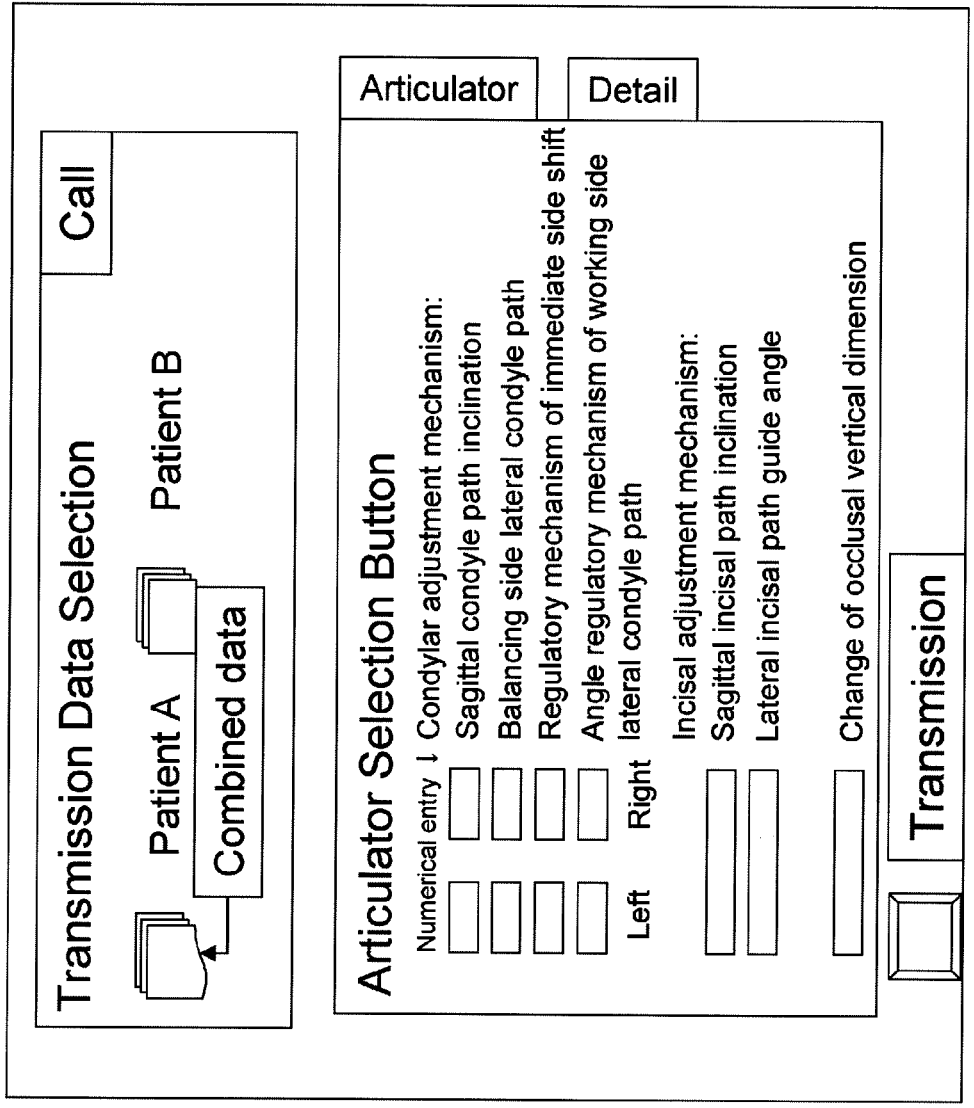
FIG. 25 is a diagram illustrating a data-transmission screen on the dentist side, where a state of forming a holder of identical jaw combined data is represented.

Next, the occlusal-surface shape data and occlusal-surface position data (post-grinding data) of occlusion-adjusted dentures, which have been received from the dentist, are overlapped with cutting data (anticipated post-grinding data) of an occlusal adjustment portion to form confirmation image data (synthetic resin) which is able to confirm whether a portion to be ground is subjected to grinding. As illustrated in FIG. 25, the combined data is stored in the holder of the transmission screen in the computer on the dentist side.

Here, examples of an overlapping method for visual confirmation include the followings:

(1) All the stereoscopic images are overlapped and made transparent.

(2) Only grinding portions are overlapped (except for portions without out grinding).

(3) Preferably, images are displayed by 3D and represented by a plane viewed from the occlusal plane.

(4) Preferably, a change in amount of data is represented by color gradation and reflected on a pre-grinding 3D data.

It is preferable to classify by color (e.g., different colors in "+" and "−" directions) whether portions of the irregular surface are at distances of 100, 50, 20 μm, preferably 10.5 μm from the cutting surface.

Figure 26:
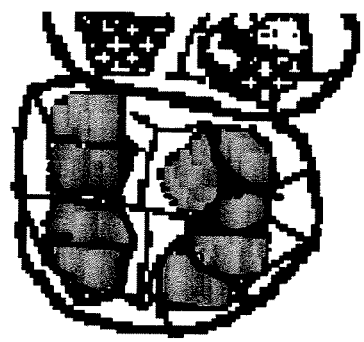
FIG. 26 is a diagram illustrating an example of a grinding surface with gradation.
Figure 27:
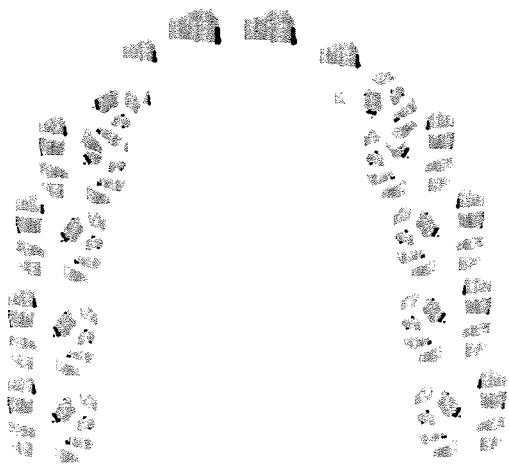
FIG. 27 is a diagram illustrating another example of a grinding surface with gradation.
Figure 28:
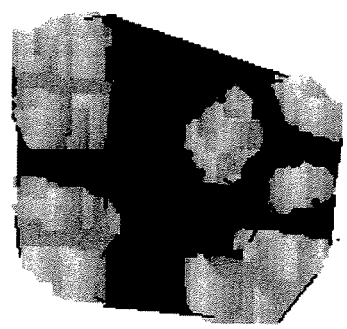
FIG. 28 is a diagram illustrating still another example of a grinding surface with gradation.

As illustrated in FIG. 26, for example, the grinding surface may be represented by color gradation on a 3D-image. Alternatively, as illustrated in FIG. 27, only a grinding surface from the occlusal surface direction may be represented by color gradation, or any portion on which grinding is not performed may be also colored as illustrated in FIG. 28.

Here, in order to reconfirm a maxillomandibular contact state, 3D-data after grinding may be moved by the above method, and it may be confirmed whether it has a contact portion. The grinding portion is not only determined by shortening (lowering) an occlusal vertical dimension but also possible to make grinding surfaces coincide with each other. It is preferable to confirm whether a new grinding surface is necessity according to the conditions of creating grinding data.

(5) Other methods include the followings:
a. A distance of arbitrary points is displayed.
b. The surface area of the grinding surface is displayed.
c. The surface area of an occlusal view is displayed.
d. The ratio of the area of a grinding surface to the area of an occlusal view is displayed.
e. The distances of grinding surfaces are classified by color and displayed.
f. The distribution of the "color classification of distances of grinding surfaces" represented in "e" is represented by a ratio.

Next, the center side observes confirmation image data and confirms whether grinding of the grinding-required portion is performed.

When the center side confirms that grinding of the grinding-required portion is finished. Then, the center side transmits confirmation image data to the dentist side. The confirmation screen used here is the same as one described in the first embodiment illustrated in FIG. 19.

The dentist side confirms that there is no problem in the confirmation image data which has been received from the grinding data provider side, and then reports this fact to the center side.

When the center side confirms that grinding of the grinding-required portion is finished, the center side creates the cutting data of a re-occlusal adjustment portion, and transmits cutting data to the dentist side.

Figure 17:
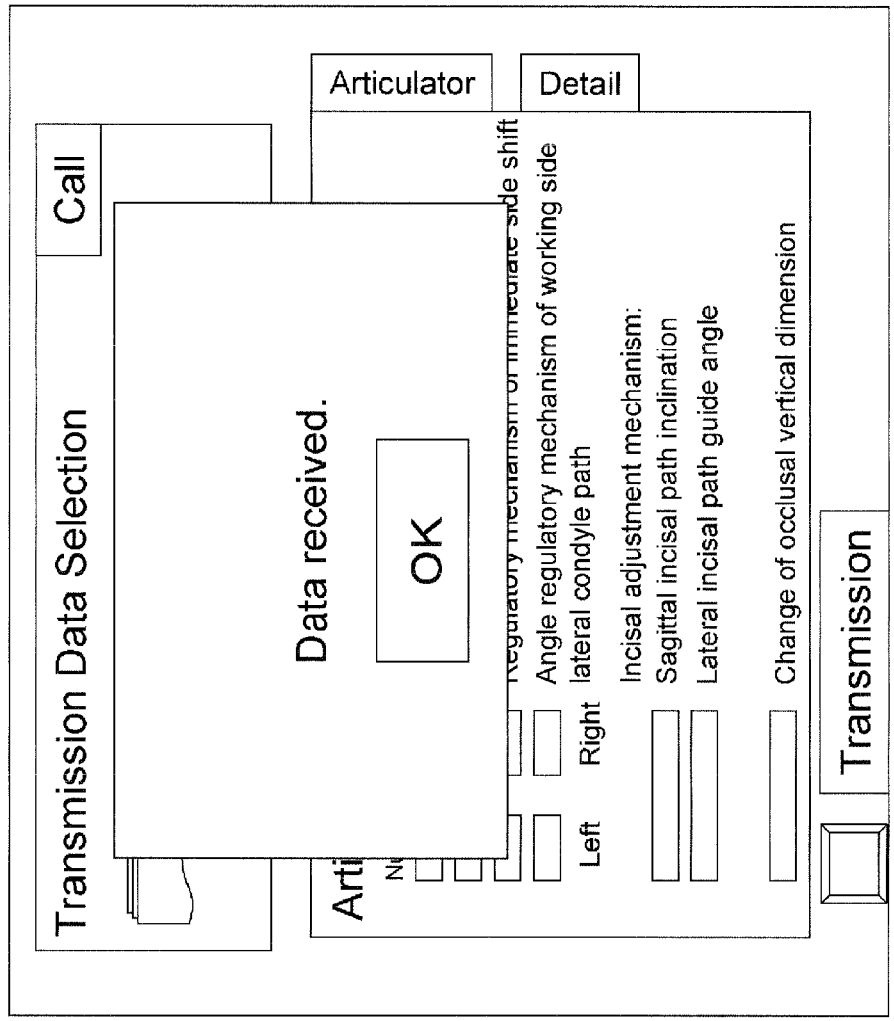
FIG. 17 is a diagram illustrating the data-transmission screen on a dentist side, where a data-acquisition message is displayed.
Figure 18:
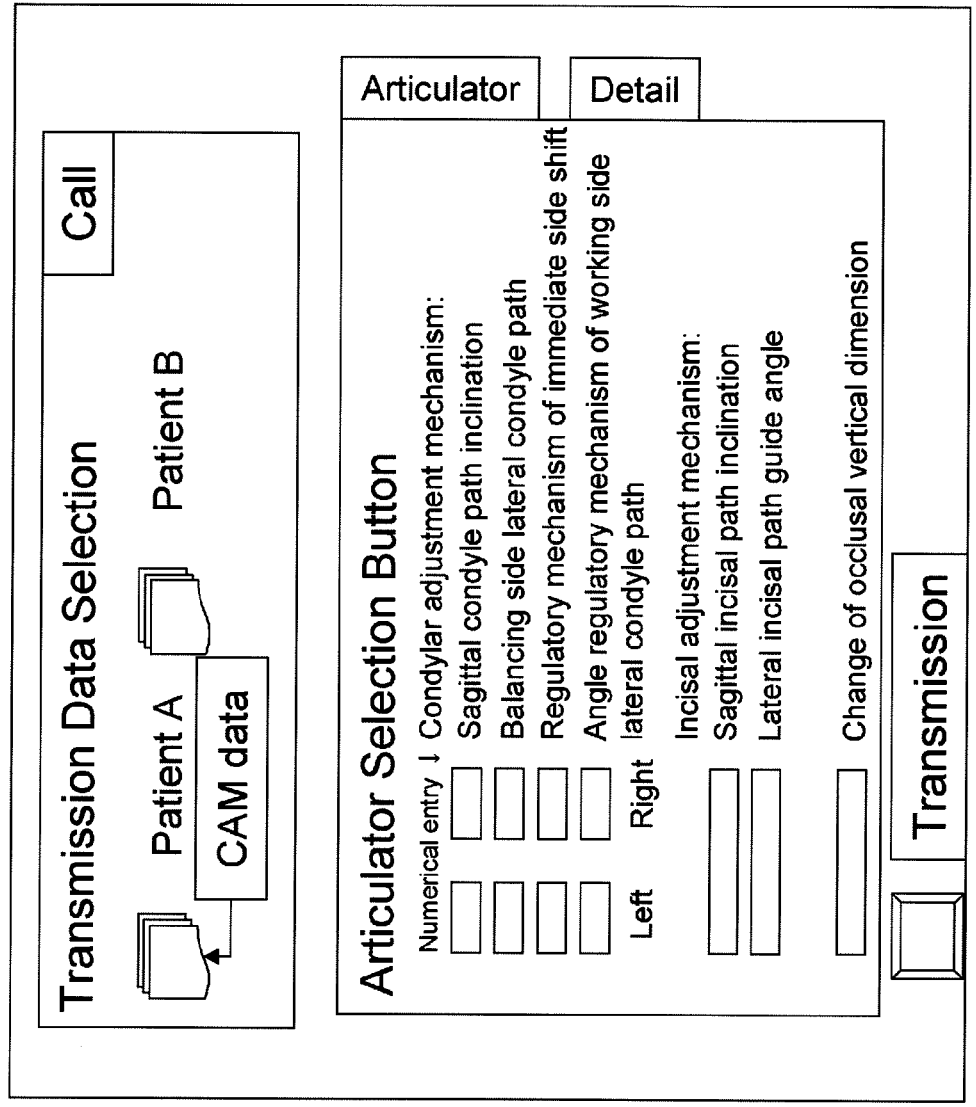
FIG. 18 is a diagram illustrating the data-transmission screen where a cutting-data stored state is displayed.

Like the first embodiment, as illustrated in FIG. 17, the dentist side allows a display side to display that cutting data is obtained.

The dentist side confirms whether a re-occlusal adjustment is necessary based on cutting data.

When the dentist side confirms that there is no need of a re-occlusal adjustment, then the dentist informs the center side that non-necessity of re-occlusal adjustment is confirmed.

When the dentist side confirms that there is a need of a re-occlusal adjustment, an occlusal adjustment is performed by cutting the dentures by a grinding machine based on the cutting data on the dentist side.

Thus, the re-occlusal adjustment is repeated until grinding of the grinding-required portion is completed.

Seventh Embodiment

Figure 14:
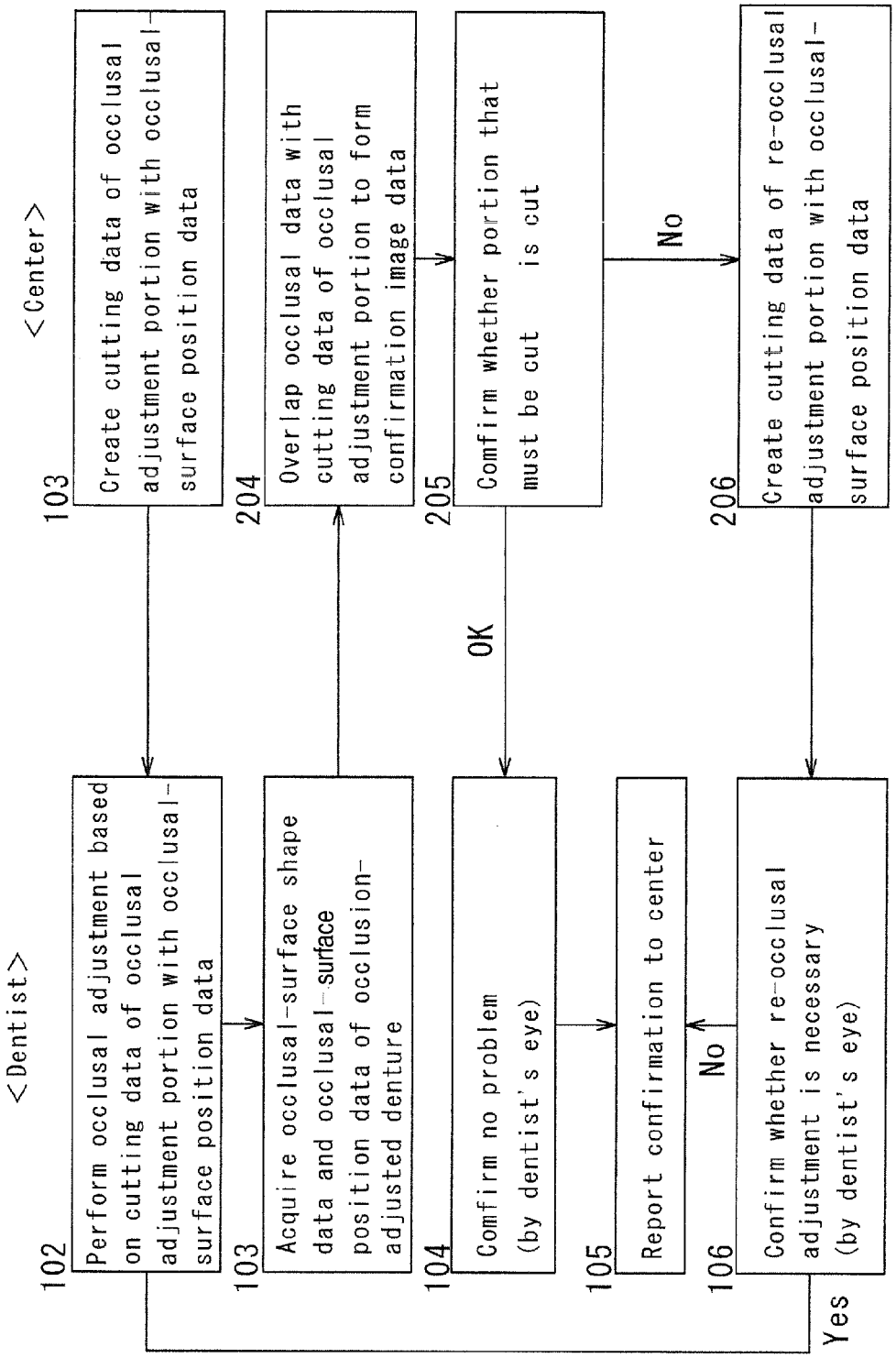
FIG. 14 is a flow chart illustrating operations on a dentist side and a center side according to a seventh embodiment.

FIG. 14 illustrates an operation of confirming an occlusal adjustment according to a seventh embodiment.

In the sixth embodiment, the center side performs confirming whether grinding of the grinding-required portion is carried out, and the dentist side accepts this. On the other hand, in the seventh embodiment, the center side transmits confirmation image data to the dentist side without confirming whether grinding of the grinding-required portion is carried out, and the dentist side diagnoses whether grinding of the grinding-required portion is finished.

For this reason, the center side transmits the created confirmation image data to the dentist side. The dentist side diagnoses whether there is no problem in the confirmation image data received from the center side.

When the dentist side concludes that there is no problem in the confirmation image data, then the dentist side reports that the dentist side has concluded no problem in confirmation image data.

When the dentist side concludes that there is a problem in confirmation image data, the center side creates cutting data of a re-occlusal adjustment portion and transmits the data to the dentist side.

The dentist side confirms whether a re-occlusal adjustment is necessary based on cutting data, when the dentist side confirms that there is no need of a re-occlusal adjustment, then the dentist side informs the center side that non-necessity of re-occlusal adjustment is confirmed. When the dentist side confirms that there is a need of a re-occlusal adjustment, an occlusal adjustment is performed by cutting the dentures by a grinding machine based on the cutting data on the dentist side.

When "diagnosing the existence of problem", the dentist may cut and adjust dentures. In this case, grinding may be performed in consideration of "color classification of distances from the cutting surface". Thus, the data can be effectively used.

The "color classification of distances from the cutting surface" may indicate the state of a food flow groove exactly, and can expect a digestion function and digestion capability (it can determine whether the dentures are the outstanding dentures). In the case where the food flow groove is absent or too small, digestion is not performed exactly. If too large, digestion efficiency can be worse. The relation of suitable dentures can be found by asking a patient about a using state of dentures or questions.

From the size and ratio of the area of an occlusal view (the maximum elevated portion seeing from the occlusal surface) and the area of a grinding surface, it can be determined whether it is easily suitable for the patient. That is, the size of a grinding surface shows the power of digesting food. Thus, when it is too large, it needs a patient's occlusal force. When it is too small, it needs to increase mastication frequency. Even if an occlusal view is too large, a patient's occlusal force is needed, while mastication frequency can be increased if too small. The relation of suitable dentures can be found by asking a patient about a using state of dentures or questions.

Eighth Embodiment

In order to reduce the amount of data to be transmitted and received between the dentist side (dentist or dental technician) and the center side, an eighth embodiment is a method for performing "transmission of occlusal-surface shape data which is a small amount of data".

Preferably, the dentist side may reduce the size of data as much as possible and then transmit the data to the center side. Likewise, the center side may reduce the size of created data and then send the data to the dentist side.

The data acquired on the dentist side requires at least "jaw-movement data", "occlusal-surface shape data", and "reference point data which connects jaw-movement data and occlusal-surface shape data". The size of each data is reduced and the data environment sent to the center side is improved.

The present method can reduce the number of data acquired on the dentist side, so that data acquisition time can be also reduced.

In order to decrease the amount of "jaw-movement data", "jaw-movement data" is considered as articulator data. Only the configuration data (condylar distance, distance between upper arch and the lower arch, sagittal condylar path inclination, balancing-side lateral condyle path angle, immediate side-shift, angle of working side lateral condyle path, sagittal incisal path inclination, and lateral incisal path guide angle) of an articulator are transmitted from the dentist side to the center side.

Preferably, the configuration data of the articulator used as a standard is transmitted.

In order to decrease the amount of "occlusal-surface shape data", 1. after acquiring occlusal-surface shape data of artificial tooth, 2. an occlusal-surface shape data of artificial tooth is verified with the artificial tooth-shape data to be used as a standard which a technician holds in advance.

3. a position in the coordinate system of occlusal-surface shape data of the reference point of the artificial tooth-shape data to be used as a standard is calculated after verification.

4. "artificial tooth-shape reference point data" of each artificial tooth is calculated, and then transmitted to a center together with "the reference point data which connects jaw-movement data and occlusal-surface shape data."

5. Transmitted "artificial tooth-shape reference point data" is compared with "artificial tooth-shape data to be used as a standard which a center holds in advance" from "the reference point data which connects jaw-movement data and occlusal-surface shape data", and then reconstituted.

Since there are 36 kinds of artificial teeth, respectively, it is preferred to have different shape reference points, respectively.

It is preferable, at the time of transmission, to divide and transmit the artificial teeth so that it may be easily recognized that reference points are classified for the respective artificial teeth (distinguishing). Since it is difficult to sufficiently match using only reference points, it is preferred to prepare several hundred occlusal surfaces for every artificial tooth. Since all are not in agreement with artificial tooth-shape data in a reference point, doubling by a rough calculation is preferred.

As a verification method of the above 2, there are two methods. One is to specify a certain portion for every artificial tooth and match the shape data with the artificial tooth-shape data and the other is to calculate a matched portion from all the acquired data. The former can reduce calculation speed, and since the latter can calculate a part automatically, operation of a worker becomes unnecessary.

Preferably, these methods may be combined to reduce work and speed.

Figure 29:
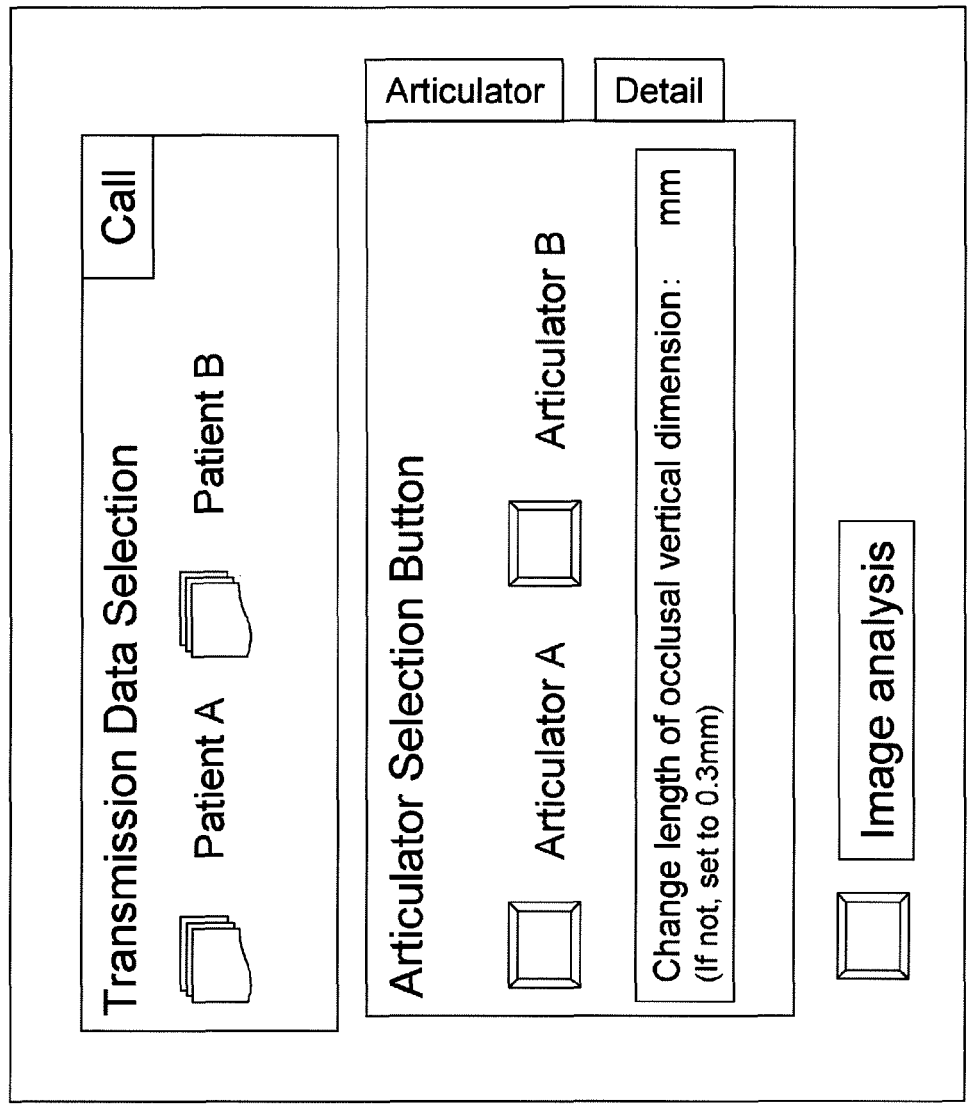
FIG. 29 is a diagram illustrating a data transmission screen on the dentist side, where an image analysis button is provided.
Figure 30:
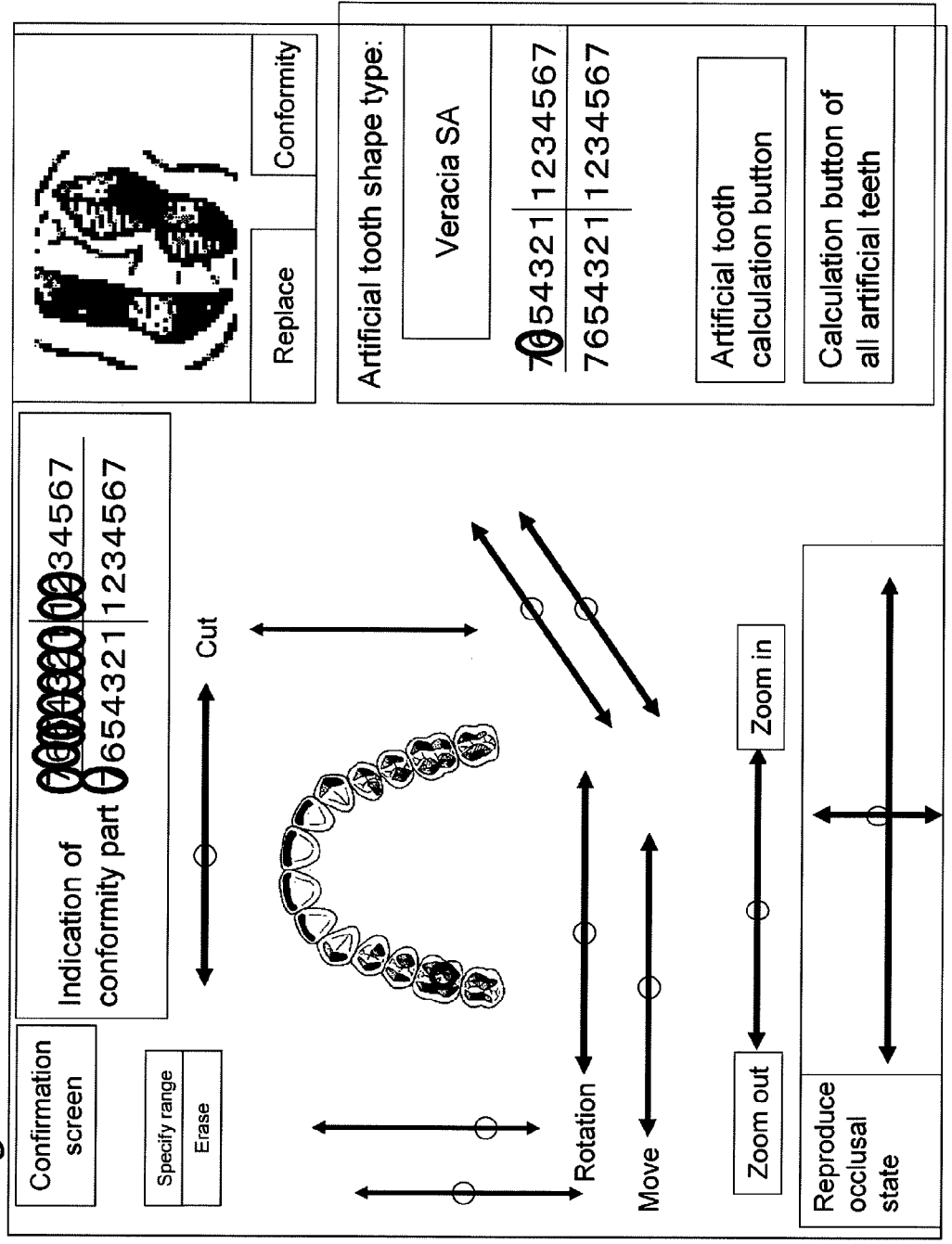
FIG. 30 is a diagram illustrating a state of confirming the conformity of an artificial tooth on a confirmation screen on the dentist side.
Figure 31:
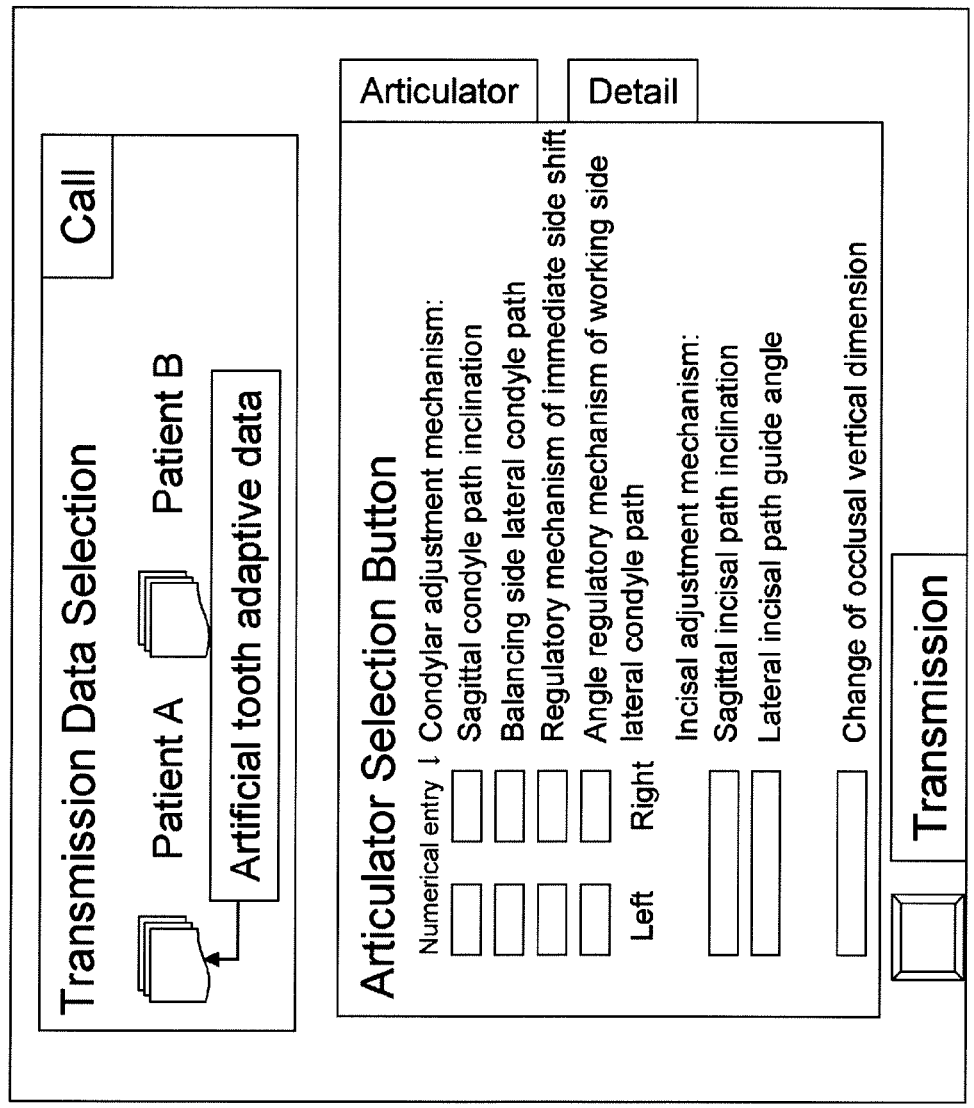
FIG. 31 is a diagram illustrating a data-transmission screen on the dentist side, where a holder of artificial tooth adaptive data is formed.

Here, the former method will be described. As illustrated in FIG. 29, on a transmission screen on the dentist side, an image-analysis button is mounted. When the image-analysis button is pressed, the conformity of artificial tooth can be seen on a confirmation screen illustrated in FIG. 30. A specific part (artificial tooth) in an image on the left side in FIG. 30 is selected and appropriate artificial tooth (Veracia SA) is selected from "artificial tooth shape type" on the right side. When "artificial tooth calculation button" is pressed, then occlusal-surface shape data and artificial tooth-shape data are verified with each other. Then, calculation is performed to determine whether occlusal-surface shape data is fit to the artificial tooth-shape data. When a conformity button on the upper right of the screen is pressed, the conformity situation of the occlusal surface can be observed. The conformity part of the artificial tooth is displayed on the upper part of the screen. When a "calculation button of all artificial teeth" on the right side of the screen is pressed, all the conformity of an artificial tooth is calculated. If the upper right button of "replace" is pressed, the conformity of next artificial tooth can be calculated. As illustrated in FIG. 31, the calculation results of the conformity are stored in a holder named artificial tooth adaptive data.

Figure 32:
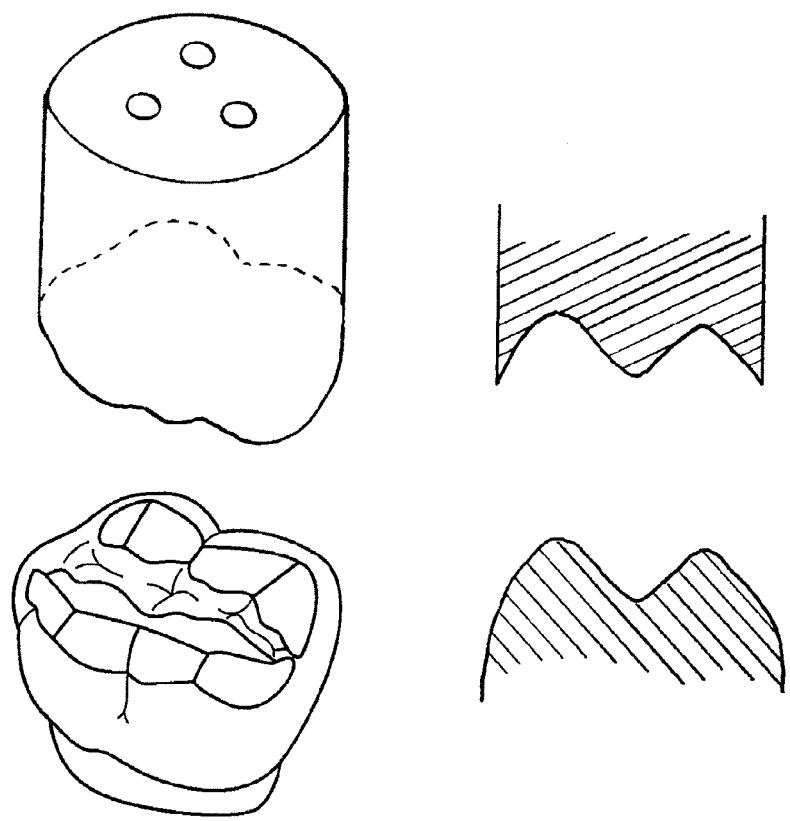
FIG. 32 is a perspective view illustrating a jig which is adapted to the occlusal surface of artificial tooth.

It is preferable to use a jig that represents the positional relationship of artificial teeth on the occlusal surface as illustrated in FIG. 32. The jig may be preferably formed so as to correspond to the shape of the occlusal surface of one tooth. The jig may be preferably in the form of a female form of the occlusal surface on which the jig can be adapted. The jig does not exceed the maximum elevated portion of artificial tooth. It is not on proximal and distal surfaces of the artificial tooth (because of hitting on the adjacent tooth).

What is claimed is:

1. A denture occlusal adjustment system, comprising:
   an acquiring unit configured to acquire three-dimensional occlusal-surface shape data and occlusal-surface position data of dentures on a dentist side, the dentures being full dentures including artificial upper teeth configured to be mounted on an upper jaw and artificial lower teeth configured to be mounted on a lower jaw;
   a first transmitter configured to transmit the occlusal-surface shape data and the occlusal-surface position data from the dentist side to a grinding data provider side;
   a reproducer configured to reproduce a maxillomandibular occlusal state on the grinding data provider side from the occlusal-surface shape data and the occlusal-surface position data received from the dentist side;
   a determining unit configured to determine a maxillomandibular occlusal adjustment portion by changing a maxillomandibular occlusal vertical dimension on the grinding data provider side;
   a preparing unit configured to prepare cutting data on the grinding data provider side, the cutting data including the maxillomandibular occlusal adjustment portion, the occlusal-surface position data, and data representative of a grinding surface which extends across an overlapped portion between three-dimensional data of one of the artificial upper teeth and one of the artificial lower teeth, the grinding surface crossing a center of gravity of the overlapped portion;
   a second transmitter configured to transmit the cutting data from the grinding data provider side to the dentist side; and
   a performing unit configured to perform an occlusal adjustment on the dentist side by cutting the dentures by a grinding machine based on the cutting data, the occlusal adjustment resulting in a ground surface on each of the artificial upper teeth and each of the artificial lower teeth that meet at a location corresponding to the grinding surface.

2. The denture occlusal adjustment system according to claim 1, further comprising:
   a creating unit configured to create image data that represents the maxillomandibular occlusal adjustment portion,
   the second transmitter being configured to transmit the image data from the grinding data provider side to the dentist side; and
   a confirming unit configured to confirm the image data received from the grinding data provider side to the dentist side and transmit a signal indicating whether the image data is accepted or not, wherein
   when the signal indicates that the image data is not accepted, the determining unit is configured to determine the maxillomandibular occlusal adjustment portion by further changing the maxillomandibular occlusal vertical dimension; and
   when the signal indicates that the image data is accepted, the creating unit is configured to create the cutting data including the occlusal-surface position data and the maxillomandibular occlusal adjustment portion.

3. The occlusal adjustment system according to claim 2, further comprising:
   a notifying unit configured to notify of a change in the maxillomandibular occlusal vertical dimension when the signal indicates that the image data is not accepted, wherein
   the determining unit is configured to determine the maxillomandibular occlusal adjustment portion at the further changed maxillomandibular occlusal vertical dimension when the notifying unit notifies of the change in the maxillomandibular occlusal vertical dimension.

4. The occlusal adjustment system according to claim 1, further comprising:
   another acquiring unit configured to acquire occlusal-surface shape data and occlusal-surface position data of occlusion-adjusted dentures on the dentist side;
   the first transmitter being configured to transmit the occlusal-surface shape data and the occlusal-surface position data of the occlusion-adjusted dentures from the dentist side to the grinding data provider side;
   a first creating unit configured to create confirmation image data for confirming whether a grinding-required portion is ground by, on the grinding data provider side, laying the occlusal-surface shape data and the occlusal-surface position data of the occlusion-adjusted dentures received from the dentist side on the cutting data including the maxillomandibular occlusal adjustment portion;
   a first confirming unit configured to confirm whether the grinding-required portion is ground on the grinding data provider side;
   the second transmitter being configured to transmit the confirmation image data from the grinding data provider side to the dentist side when confirming that the grinding-required portion is ground;
   a second confirming unit configured to confirm whether the confirmation image data received from the grinding data provider side by the dentist side has a problem;
   a first notifying unit configured to notify a center side from the dentist side that no problem in the confirmation image data is confirmed;
   a second creating unit configured to create cutting data of a re-occlusal adjustment portion on the grinding data provider side when confirmation that the grinding-required portion is ground is obtained;
   the second transmitter being configured to transmit the cutting data from the grinding data provider side to the dentist side;
   a third confirming unit configured to confirm whether re-occlusal adjustment is required based on the cutting data on the dentist side; and
   a second notifying unit configured to notify that no need of re-occlusal adjustment is confirmed when the dentist side confirms no need of re-occlusal adjustment, wherein
   when the third confirming unit confirms that re-occlusal adjustment is required, an occlusal adjustment is performed by cutting the dentures on the dentist side by a grinding machine based on the cutting data.

5. The denture occlusal adjustment system according to claim 1, further comprising:
   another acquiring unit configured to acquire occlusal-surface shape data and occlusal-surface position data of occlusion-adjusted dentures on the dentist side;
   the first transmitter being configured to transmit the occlusal-surface shape data and the occlusal-surface position data of the occlusion-adjusted dentures from the dentist side to the grinding data provider side;
a first creating unit configured to create confirmation image data for confirming whether a grinding-required portion is ground by, on the grinding data provider side, laying the occlusal-surface shape data and the occlusal-surface position data of the occlusion-adjusted dentures received from the dentist side on the cutting data including the maxillomandibular occlusal adjustment portion;
the second transmitter being configured to transmit the confirmation image data from the grinding data provider side to the dentist side;
a diagnosing unit configured to diagnose whether the confirmation image data received from the grinding data provider side by the dentist side has a problem;
a first notifying unit configured to notify from the dentist side that no problem exists in the confirmation image data when no problem is found during the diagnosing of the confirmation image data;
a second creating unit configured to create cutting data of a re-occlusal adjustment portion on the grinding data provider side when a problem in the confirmation image data is diagnosed;
the second transmitter being configured to transmit the cutting data from the grinding data provider side to the dentist side; and
a confirming unit configured to confirm whether re-occlusal adjustment is required based on the cutting data on the dentist side; and
a second notifying unit configured to notify that no need of re-occlusal adjustment is confirmed when the dentist side confirms no need of re-occlusal adjustment, wherein
when the confirming unit confirms that re-occlusal adjustment is required, an occlusal adjustment is performed by cutting the dentures on the dentist side by a grinding machine based on the cutting data.

6. The denture occlusal adjustment system according to claim 5, wherein:
the jaw-movement data is set data of an articulator including a condylar distance, a distance between an upper arch and a lower arch, a sagittal condylar path inclination, a balancing-side lateral condyle path angle, an immediate side shift, an angle of a working side lateral condyle path, a sagittal incisal path inclination, and a lateral incisal path guide angle.

7. The denture occlusal adjustment system according to claim 5, further comprising:
a calculating unit configured to calculate artificial tooth-shape reference point data to be used as a standard by making a verification between the acquired occlusal-surface shape data of one of the artificial upper teeth and artificial lower teeth and the artificial tooth-shape data to be used as the standard, wherein
the first transmitter is configured to transmit the artificial tooth-shape reference point data as the occlusal-surface shape data, and further includes:
a reconstructing unit configured to reconstruct occlusal-surface shape data of one of the artificial upper teeth and artificial lower teeth and verify the artificial tooth-shape reference point data with a reference point of artificial tooth-shape data to be used as a standard on the grinding data provider side.

8. The denture occlusal adjustment system according to claim 1, wherein the acquiring unit is configured to acquire, in addition to the occlusal-surface shape data and the occlusal-surface position data, jaw-movement data and reference point data that makes a connection between the jaw-movement data and the occlusal-surface shape data.

9. A denture occlusal adjustment system, comprising:
an acquiring unit configured to acquire three-dimensional maxillomandibular impression data with silicone or wax on a dentist side;
a first transmitter configured to transmit the maxillomandibular impression data from the dentist side to a grinding data provider side;
a reproducer configured to reproduce a maxillomandibular occlusal state on the grinding data provider side from the maxillomandibular impression data received from the dentist side;
a determining unit configured to determine a maxillomandibular occlusal adjustment portion by changing a maxillomandibular occlusal vertical dimension on the grinding data provider side;
a preparing unit configured to prepare cutting data on the grinding data provider side, the cutting data including the maxillomandibular occlusal adjustment portion, the maxillomandibular impression data, and data representative of a grinding surface which extends across an overlapped portion between three-dimensional data of one of the artificial upper teeth and one of the artificial lower teeth, the grinding surface crossing a center of gravity of the overlapped portion;
a second transmitter configured to transmit the cutting data from the grinding data provider side to the dentist side; and
a performing unit configured to perform an occlusal adjustment on the dentist side by cutting dentures by a grinding machine based on the cutting data, the dentures being full dentures including artificial upper teeth configured to be mounted on an upper jaw and artificial lower teeth configured to be mounted on a lower jaw, and the occlusal adjustment resulting in a ground surface on each of the artificial upper teeth and the artificial lower teeth that meet at a location corresponding to the grinding surface.

10. The denture occlusal adjustment system according to claim 9, further comprising:
a creating unit configured to create image data that represents the maxillomandibular occlusal adjustment portion,
the second transmitter being configured to transmit the image data from the grinding data provider side to the dentist side; and
a confirming unit configured to confirm the image data received from the grinding data provider side to the dentist side and transmit a signal indicating whether the image data is accepted or not, wherein
when the signal indicates that the image data is not accepted, the determining unit is configured to determine the maxillomandibular occlusal adjustment portion by further changing the maxillomandibular occlusal vertical dimension; and
when the signal indicates that the image data is accepted, the creating unit is configured to create the cutting data including the occlusal-surface position data and the maxillomandibular occlusal adjustment portion.

* * * * *